(12) United States Patent
Lee et al.

(10) Patent No.: US 10,765,564 B2
(45) Date of Patent: Sep. 8, 2020

(54) FLEXIBLE ABSORBENT ARTICLE WITH A LOBED ABSORBENT LAYER

(71) Applicant: Kimberly-Clark Worldwide, Inc., Neenah, WI (US)

(72) Inventors: JuHyung Lee, Gangnam-gu (KR); SungSu A. Kim, Gangnam-gu (KR); MoonYoung Cho, Yongin-si (KR); SeoYeon Son, Gangnam-gu (KR); HyungWoo Park, Gangnam-gu (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 435 days.

(21) Appl. No.: 15/575,177

(22) PCT Filed: May 29, 2015

(86) PCT No.: PCT/US2015/033218
§ 371 (c)(1),
(2) Date: Nov. 17, 2017

(87) PCT Pub. No.: WO2016/195632
PCT Pub. Date: Dec. 8, 2016

(65) Prior Publication Data
US 2018/0140476 A1 May 24, 2018

(51) Int. Cl.
*A61F 13/47* (2006.01)
*A61F 13/472* (2006.01)
(Continued)

(52) U.S. Cl.
CPC .... *A61F 13/4704* (2013.01); *A61F 13/15203* (2013.01); *A61F 13/47218* (2013.01);
(Continued)

(58) Field of Classification Search
CPC .............. A61F 13/4702; A61F 13/4704; A61F 13/47236; A61F 13/47245; A61F 13/4757; A61F 13/476; A61F 13/4727; A61F 2013/51078; A61F 2013/5108; A61F 2013/51083; A61F 2013/51085
See application file for complete search history.

(56) References Cited

U.S. PATENT DOCUMENTS

| | | |
|---|---|---|
| 4,357,939 A | 11/1982 | Jackson |
| 4,701,178 A | 10/1987 | Glaug |

(Continued)

FOREIGN PATENT DOCUMENTS

| | | |
|---|---|---|
| CN | 1080164 A | 1/1994 |
| CN | 1191105 A | 8/1998 |

(Continued)

*Primary Examiner* — Catharine L Anderson
*Assistant Examiner* — Lynne Anderson
(74) *Attorney, Agent, or Firm* — Kimberly-Clark Worldwide, Inc.

(57) ABSTRACT

An absorbent article can have a chassis which can have a backsheet layer, a topsheet layer, and an absorbent system positioned between the backsheet layer and the topsheet layer. The absorbent system can have at least one absorbent layer which is a lobed absorbent layer. At least one flexure feature can associate with the lobed absorbent layer. A pair of non-integral wings can be bonded to the backsheet layer of the chassis.

12 Claims, 24 Drawing Sheets

(51) Int. Cl.
*A61F 13/515* (2006.01)
*A61F 13/56* (2006.01)
*A61F 13/511* (2006.01)
*A61F 13/537* (2006.01)
*A61F 13/15* (2006.01)

(52) U.S. Cl.
CPC .. *A61F 13/47236* (2013.01); *A61F 13/47272* (2013.01); *A61F 13/515* (2013.01); *A61F 13/51108* (2013.01); *A61F 13/537* (2013.01); *A61F 13/5611* (2013.01); *A61F 13/5616* (2013.01); *A61F 2013/15292* (2013.01)

(56) References Cited

U.S. PATENT DOCUMENTS

| | | | |
|---|---|---|---|
| 4,900,320 A | 2/1990 | McCoy | |
| 5,080,658 A | 1/1992 | Igaue | |
| 5,133,705 A | 7/1992 | Nakanishi | |
| 5,201,727 A | 4/1993 | Nakanishi | |
| 5,387,210 A | 2/1995 | Murakami | |
| 5,490,847 A | 2/1996 | Correa et al. | |
| 5,514,104 A | 5/1996 | Cole | |
| 5,620,430 A | 4/1997 | Bamber | |
| 5,643,245 A | 7/1997 | Osborn et al. | |
| 5,713,884 A | 2/1998 | Osborn | |
| 5,718,699 A | 2/1998 | Brisebois | |
| 5,766,389 A | 6/1998 | Brandon | |
| 5,772,650 A | 6/1998 | Mizutani | |
| 5,860,965 A | 1/1999 | Lavash | |
| 5,932,039 A | 8/1999 | Popp | |
| 5,951,536 A | 9/1999 | Osborn | |
| 5,961,505 A | 10/1999 | Coe | |
| 6,013,066 A | 1/2000 | Samuelsson | |
| 6,117,523 A | 9/2000 | Sugahara | |
| 6,264,640 B1 | 7/2001 | Sutton | |
| 6,309,378 B1 | 10/2001 | Costa | |
| 6,387,074 B1 | 5/2002 | Horppu et al. | |
| 6,394,990 B1 | 5/2002 | Rosenfeld | |
| 6,436,080 B1 | 8/2002 | Carlucci | |
| 6,461,339 B1 | 10/2002 | Sugahara | |
| 6,464,675 B2 | 10/2002 | de Carvalho | |
| 6,602,236 B1 | 8/2003 | Mizutani | |
| 6,617,490 B1 | 9/2003 | Chen | |
| 6,652,686 B1 | 11/2003 | Coenen | |
| 6,659,991 B2 | 12/2003 | Suekane | |
| 6,749,594 B2 | 6/2004 | Hansson | |
| 6,932,798 B2 | 8/2005 | Kudo | |
| 7,056,311 B2 | 6/2006 | Kinoshita | |
| 7,078,583 B2 | 7/2006 | Kudo | |
| 7,156,832 B2 * | 1/2007 | Drevik | A61F 13/4702 604/379 |
| 7,163,529 B2 * | 1/2007 | Mocadlo | A61F 13/4755 604/359 |
| 7,166,093 B2 * | 1/2007 | Drevik | A61F 13/47272 604/385.01 |
| 8,048,049 B2 | 11/2011 | Fujikawa | |
| 8,157,780 B2 | 4/2012 | Lira | |
| 8,211,074 B2 | 7/2012 | Ohba | |
| 8,293,966 B2 | 10/2012 | Obele | |
| 8,343,123 B2 | 1/2013 | Noda et al. | |
| 8,366,696 B2 * | 2/2013 | Konawa | A61F 13/15764 604/365 |
| 8,461,411 B2 | 6/2013 | Digiacomantonio et al. | |
| 8,486,037 B2 | 7/2013 | Konawa | |
| 8,563,802 B2 | 10/2013 | Nishikawa | |
| 8,684,985 B2 | 4/2014 | Odoi | |
| 9,308,135 B2 | 4/2016 | You | |
| 2002/0013563 A1 | 1/2002 | Lassen | |
| 2002/0040215 A1 | 4/2002 | Suzuki | |
| 2002/0156443 A1 | 10/2002 | Drevik et al. | |
| 2003/0004484 A1 | 1/2003 | Hammons | |
| 2003/0055392 A1 | 3/2003 | Tagami | |
| 2004/0015145 A1 | 1/2004 | Miura | |
| 2004/0133179 A1 | 7/2004 | Steger | |
| 2005/0131372 A1 | 6/2005 | Wheeler et al. | |
| 2005/0137556 A1 | 6/2005 | Brisebois | |
| 2005/0187531 A1 | 8/2005 | Alcantara | |
| 2005/0256472 A1 * | 11/2005 | Tsutsui | A61F 13/47263 604/378 |
| 2006/0025736 A1 | 2/2006 | Berg | |
| 2007/0100308 A1 | 5/2007 | Miyairi | |
| 2009/0062761 A1 | 3/2009 | Goerg-Wood | |
| 2010/0191210 A1 | 7/2010 | Hayashi | |
| 2010/0298800 A1 | 11/2010 | Berg, Jr. | |
| 2010/0305738 A1 | 12/2010 | DeBruler | |
| 2011/0264067 A1 | 10/2011 | Rubio | |
| 2012/0004633 A1 | 1/2012 | Marcelo | |
| 2012/0136327 A1 | 5/2012 | Jones | |
| 2012/0215195 A1 | 8/2012 | Lira | |
| 2012/0253305 A1 | 10/2012 | Noel | |
| 2012/0265162 A1 | 10/2012 | Kuramochi | |
| 2012/0302984 A1 | 11/2012 | Lavash | |
| 2013/0110070 A1 | 5/2013 | Nakaoka | |
| 2013/0123729 A1 | 5/2013 | Minami | |
| 2015/0080831 A1 | 3/2015 | Munakata | |
| 2018/0140475 A1 | 5/2018 | Lee | |

FOREIGN PATENT DOCUMENTS

| | | | |
|---|---|---|---|
| CN | 1426768 A | 7/2003 | |
| CN | 1809327 A | 7/2006 | |
| CN | 101686886 A | 3/2010 | |
| EP | 0550736 A1 | 7/1993 | |
| EP | 0764433 A1 | 3/1997 | |
| EP | 0923921 A1 | 6/1999 | |
| EP | 0689821 B1 | 2/2000 | |
| EP | 1208823 A1 | 5/2002 | |
| GB | 2244653 B2 | 9/1994 | |
| JP | 3812812 B2 | 8/2006 | |
| JP | 4836639 B2 | 12/2011 | |
| JP | 5164390 B2 | 3/2013 | |
| JP | 5520630 B2 | 6/2014 | |
| JP | 5596516 B2 | 9/2014 | |
| MX | PA03000102 A1 | 10/2004 | |
| WO | 9741818 A1 | 11/1997 | |
| WO | 9855063 A1 | 12/1998 | |
| WO | 03086257 A1 | 10/2003 | |
| WO | 08029558 A1 | 3/2008 | |
| WO | 11096483 A1 | 8/2011 | |
| WO | 12057332 A1 | 5/2012 | |
| WO | WO-2013070190 A1 * | 5/2013 | ......... A61F 13/4702 |
| WO | 14078247 A2 | 5/2014 | |
| WO | 14171861 A1 | 10/2014 | |

* cited by examiner

FLEXIBLE ABSORBENT ARTICLE WITH A LOBED ABSORBENT LAYER

BACKGROUND

Products such as absorbent articles are often used to collect and retain human body exudates containing, for example, urine, menses and/or blood. Comfort, absorbency, and discretion are three main areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a wearer-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wings for wrapping about the wearer's undergarment to further secure the product to the undergarment and to protect the undergarment from staining. Such wings (also known as flaps or tabs) are frequently made from lateral extensions of the topsheet and/or backsheet layers.

Such products, however, can have drawbacks which can detract from the comfort, absorbency and discretion sought by the wearer of the product. For example, a common problem with such products is their tendency to bunch, twist, and/or distort during usage. This is a common complaint among wearers resulting in overall dissatisfaction with the product despite its absorbent capabilities. An additional drawback is that the peripheral seal between the topsheet layer and the backsheet layer can irritate the skin of the wearer which can be exacerbated by any additional distortion, bunching, and/or twisting of the product.

There remains a need for an improved product, such as an absorbent article, that can have minimal distortion, bunching and/or twisting in the undergarment of the wearer. There remains a need for an improved product, such as an absorbent article, that can cause minimal irritation to the wearer's skin during usage of the absorbent article.

SUMMARY

In various embodiments, an absorbent article can have a longitudinal direction, a transverse direction, and a depth direction; a longitudinal axis and a transverse axis wherein the absorbent article is asymmetrical about the transverse axis; a chassis comprising: a first transverse direction end edge and a second transverse direction end edge; a topsheet layer comprising a first longitudinal direction peripheral edge and a second longitudinal direction peripheral edge; a backsheet layer comprising a first longitudinal direction peripheral edge and a second longitudinal direction peripheral edge; an absorbent system positioned between the topsheet layer and the backsheet layer, the absorbent system comprising a garment facing surface, a wearer facing surface, a first longitudinal direction peripheral region and a second longitudinal direction peripheral region, and at least two absorbent layers, wherein at least one of the absorbent layers of the absorbent system is a lobed absorbent layer comprising a first lobe and a second lobe wherein the first and second lobe define a longitudinally extending void space in the absorbent layer; a first longitudinal direction bond region wherein the first longitudinal direction peripheral edge of the topsheet layer is bonded to the first longitudinal direction peripheral edge of the backsheet layer; and a second longitudinal direction bond region wherein the second longitudinal direction peripheral edge of the topsheet layer is bonded to the second longitudinal direction peripheral edge of the backsheet layer; at least one flexure feature wherein the at least one flexure feature comprises at least one flexure element extending in a direction generally parallel to the longitudinal axis and wherein the at least one flexure element is positioned within the void space; and a first non-integral wing and a second non-integral wing, each of the first and second non-integral wings bonded to the backsheet layer.

In various embodiments, the absorbent article can further have a first side cover bonded to the chassis in the region of the first longitudinal direction bond region and a second side cover bonded to the chassis in the region of the second longitudinal direction bond region. In various embodiments, each of the first side cover and the second side cover is bonded to an exterior surface of the backsheet layer. In various embodiments, each of the first side cover and the second side cover extend between the first transverse direction end edge and the second transverse direction end edge of the chassis. In various embodiments, each of the first side cover and the second side cover have at least one concave region and at least convex region.

In various embodiments, the first non-integral wing and the second non-integral wing are separate components from each other. In various embodiments, the first non-integral wing and the second non-integral wing are integral with a bridge which is bonded to the backsheet layer.

In various embodiments, at least one of the first transverse direction end edge and the second transverse direction end edge has at least one concave region. In various embodiments, the first transverse direction end edge and the second transverse direction end edge form a nesting configuration.

In various embodiments, the at least one flexure feature comprises a second flexure element, the second flexure element spaced in the transverse direction outward from the first flexure element and positioned at an angle relative to the longitudinal axis. In various embodiments, the second flexure element is aligned with an interior side edge of at least one of the lobes of the lobed absorbent layer. In various embodiments, the absorbent article further has a garment attachment on an exterior surface of the backsheet layer wherein the backsheet layer is substantially free of the garment attachment in an area of the backsheet layer positioned below the flexure feature in the depth direction of the absorbent article.

In various embodiments, the absorbent system further comprises at least one additional layer selected from a surge layer, a fluid intake layer, a transfer delay layer and a distribution layer.

In various embodiments, the absorbent article further comprises a transversely extending void space within the lobed absorbent layer. In various embodiments, the absorbent article further has a secondary flexure feature extending in a direction generally parallel to the transverse axis and positioned within the transversely extending void space.

DETAILED DESCRIPTION

Figure 1:
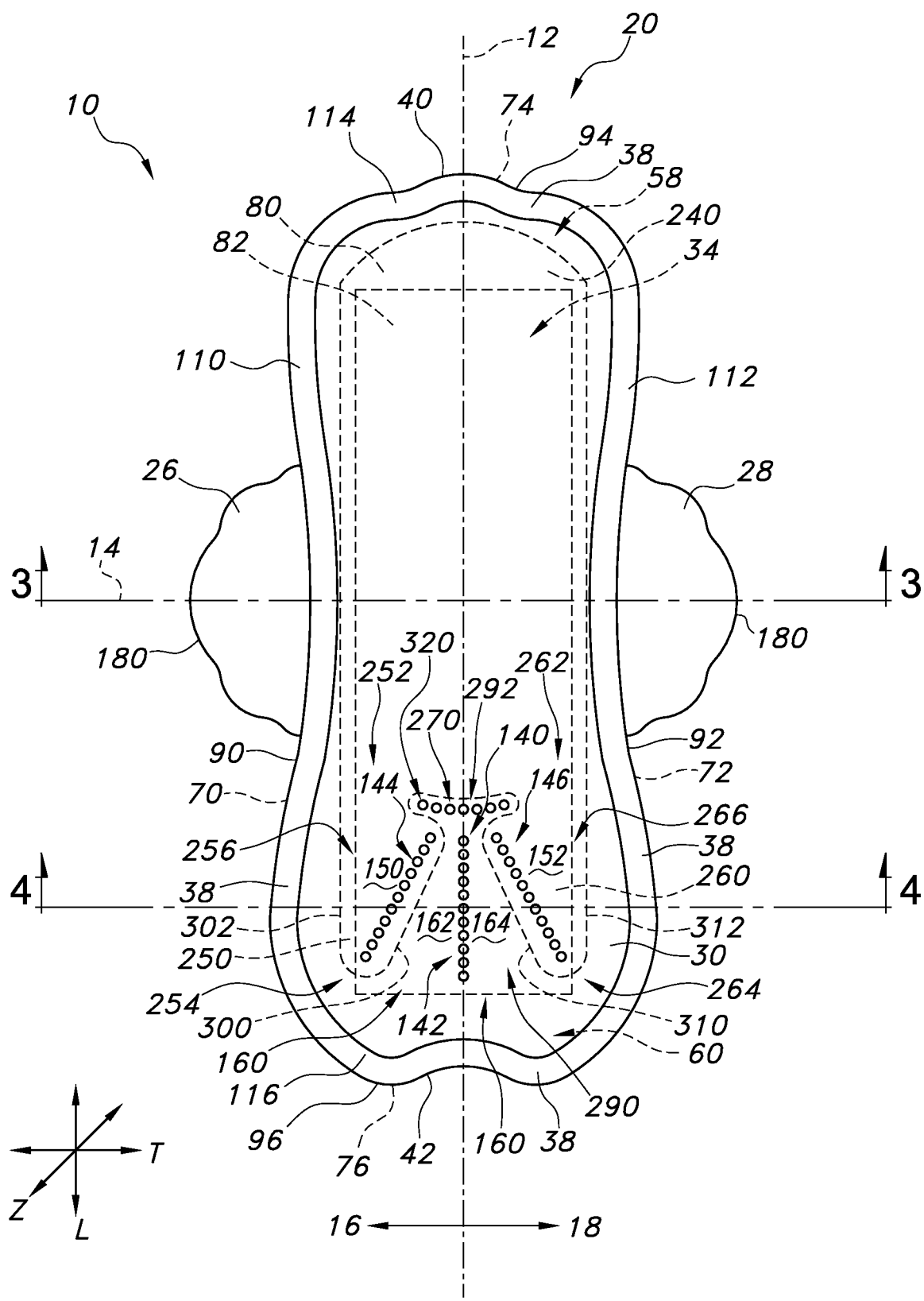
FIG. 1 is a top view of an embodiment of an absorbent article.

The present disclosure is generally directed towards a flexible absorbent article which can have an improved resistance to bunching, twisting and/or distortion and which can have a reduction in irritation to a wearer's skin during usage of the absorbent article. The absorbent article can have a chassis, a lobed absorbent layer within the chassis, a flexure feature, and a pair of non-integral wings. In various embodiments, the absorbent article can further have a pair of non-integral side covers. The chassis of the absorbent article can have a topsheet layer, a backsheet layer, and an absorbent system positioned between the topsheet layer and the backsheet layer. The topsheet layer and the backsheet layer can overlay each other and can be bonded together to form a seal between the topsheet layer and the backsheet layer in order to contain the absorbent system and body exudates received into the chassis through the topsheet layer. At least one layer of the absorbent system can be a lobed absorbent layer and the flexure feature can be associated with the lobed absorbent layer. The configuration of the lobed absorbent layer and the positioning of the flexure feature can provide a flexed, raised and tented configuration to the absorbent article which can be comfortable to wear and which can maintain proper placement for the wearer of the absorbent article. The configuration of the lobed absorbent layer and the positioning of the flexure feature can determine the extent of the tenting configuration. The configuration of the lobed absorbent layer and the positioning of the flexure feature can help maintain the absorbent article in a flexed, raised and tented configuration. The non-integral wings can be bonded to the backsheet layer of the chassis and can extend in a transverse direction of the absorbent article.

Definitions:

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter.

Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Absorbent Article:

The present disclosure is generally directed towards a flexible absorbent article which can have an improved resistance to bunching, twisting and/or distortion and which can have a reduction in irritation to a wearer's skin during usage of the absorbent article. The flexible absorbent article can have a chassis, a lobed absorbent layer within the chassis, and a pair of non-integral wings. In various embodiments, the absorbent article can further have a pair of non-integral side covers. The chassis of the absorbent article can have a topsheet layer, a backsheet layer, and an absorbent system positioned between the topsheet layer and the backsheet layer. The topsheet layer and the backsheet layer can overlay each other and can be bonded together to form a seal between the topsheet layer and the backsheet layer in order to contain the absorbent system and body exudates received into the chassis through the topsheet layer. At least one layer of the absorbent system can be a lobed absorbent layer and the flexure feature can be associated with the lobed absorbent layer. The configuration of the lobed absorbent layer and the positioning of the flexure feature can provide a flexed, raised and tented configuration to the absorbent article which can be comfortable to wear and which can maintain proper placement for the wearer of the absorbent article. The configuration of the lobed absorbent layer and the positioning of the flexure feature can determine the extent of the tenting configuration. The configuration of the lobed absorbent layer and the positioning of the flexure feature can help maintain the absorbent article in a flexed, raised and tented configuration. The non-integral wings can be bonded to the backsheet layer of the chassis and can extend in a transverse direction of the absorbent article.

Figure 2:
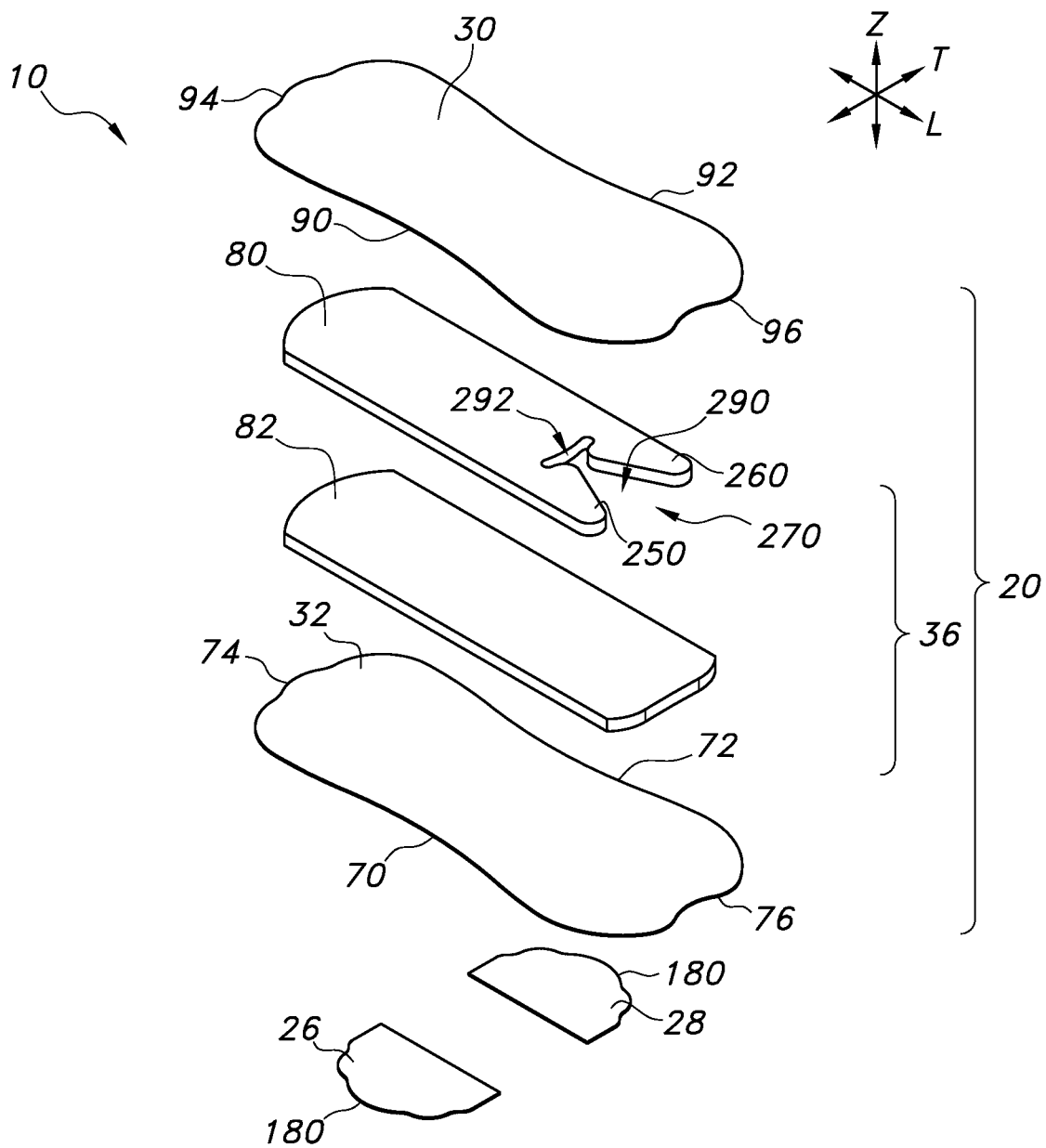
FIG. 2 is an exploded perspective view of the absorbent article of FIG. 1.
Figure 3:
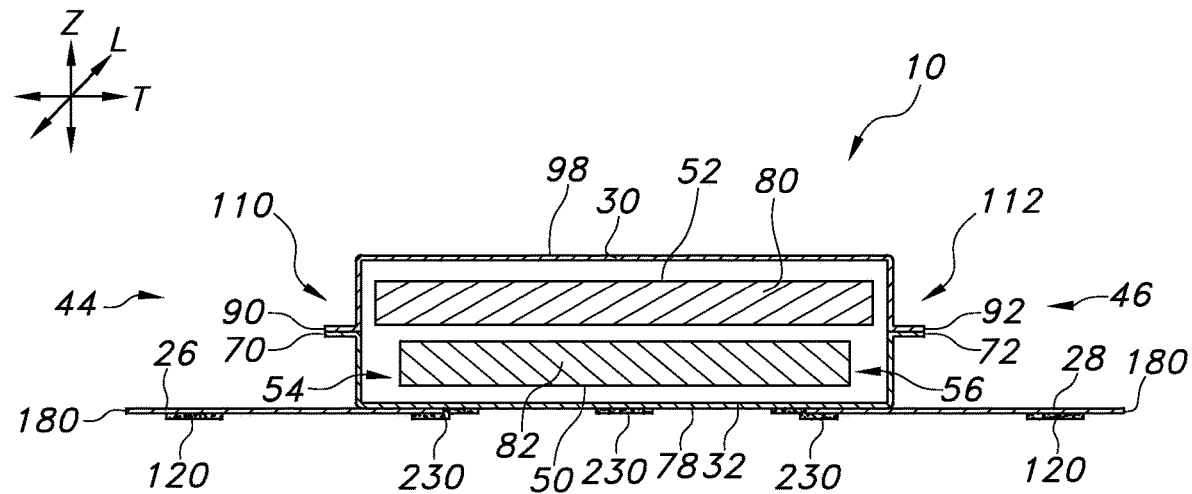
FIG. 3 is an exploded cross-sectional view of the absorbent article of FIG. 1 taken along line 3-3.
Figure 4:
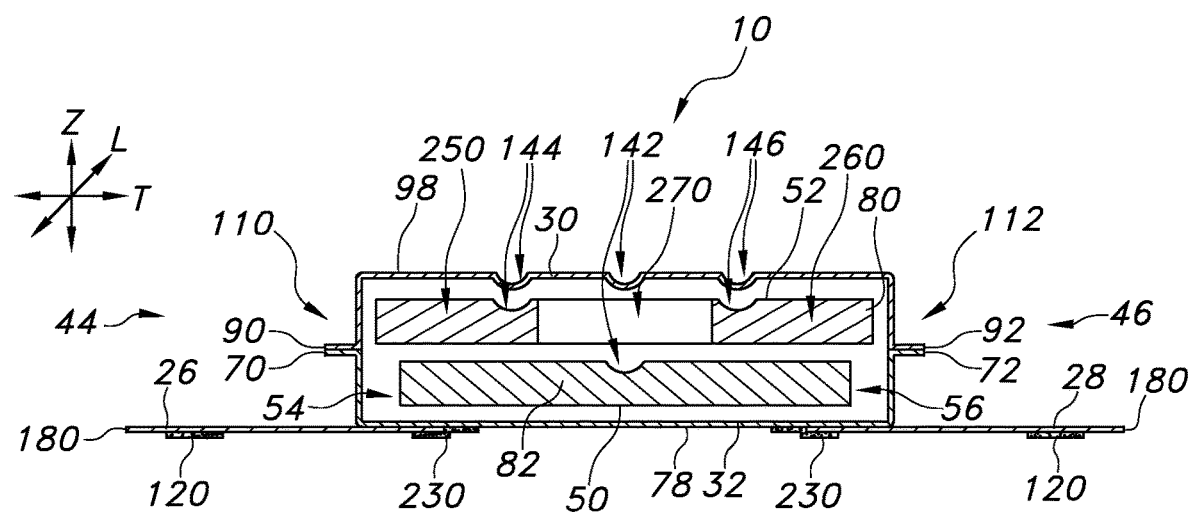
FIG. 4 is an exploded cross-sectional view of the absorbent article of FIG. 1 taken along line 4-4.
Figure 5:
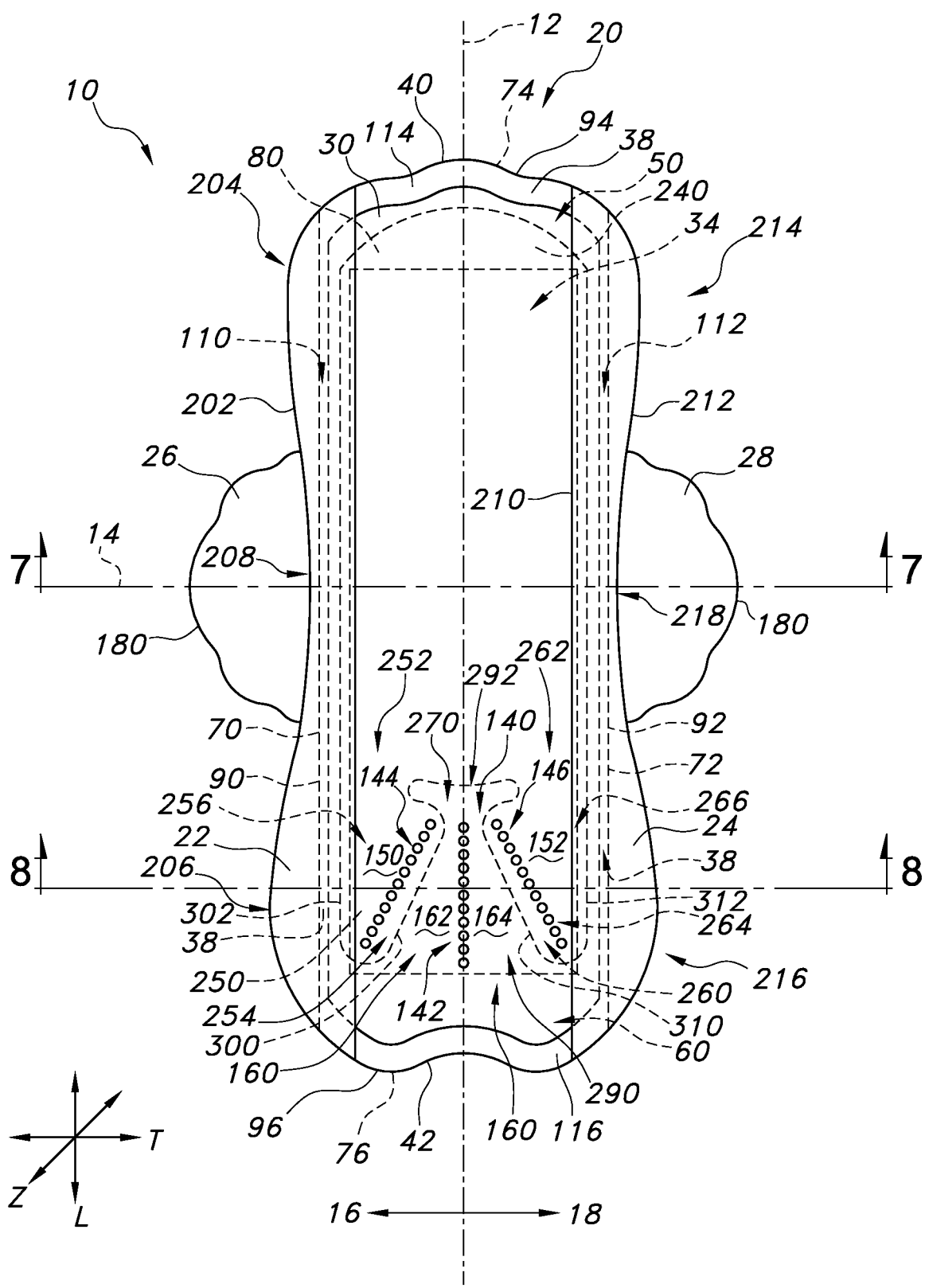
FIG. 5 is a top view of an embodiment of an absorbent article.
Figure 6:
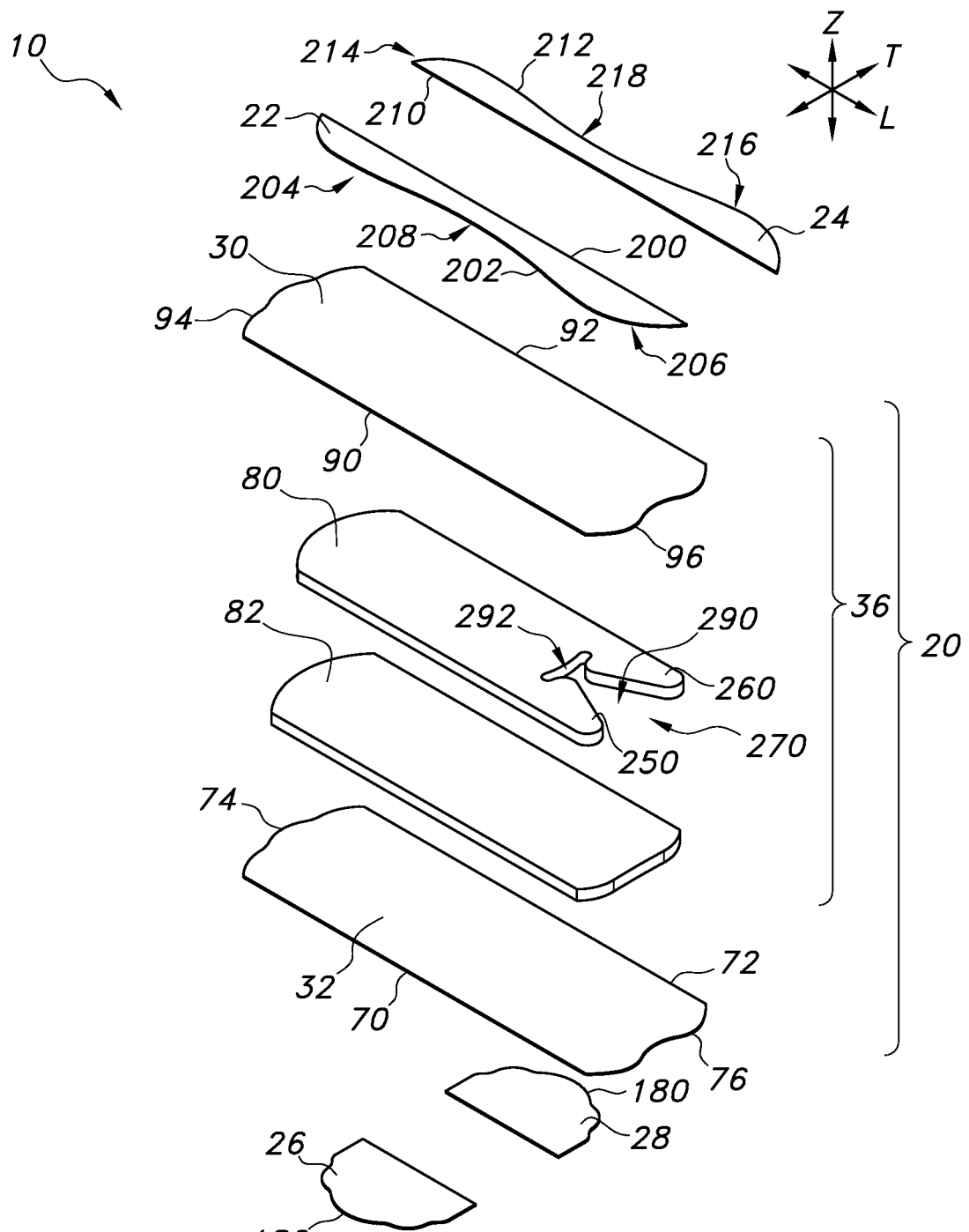
FIG. 6 is an exploded perspective view of the absorbent article of FIG. 5.
Figure 7:
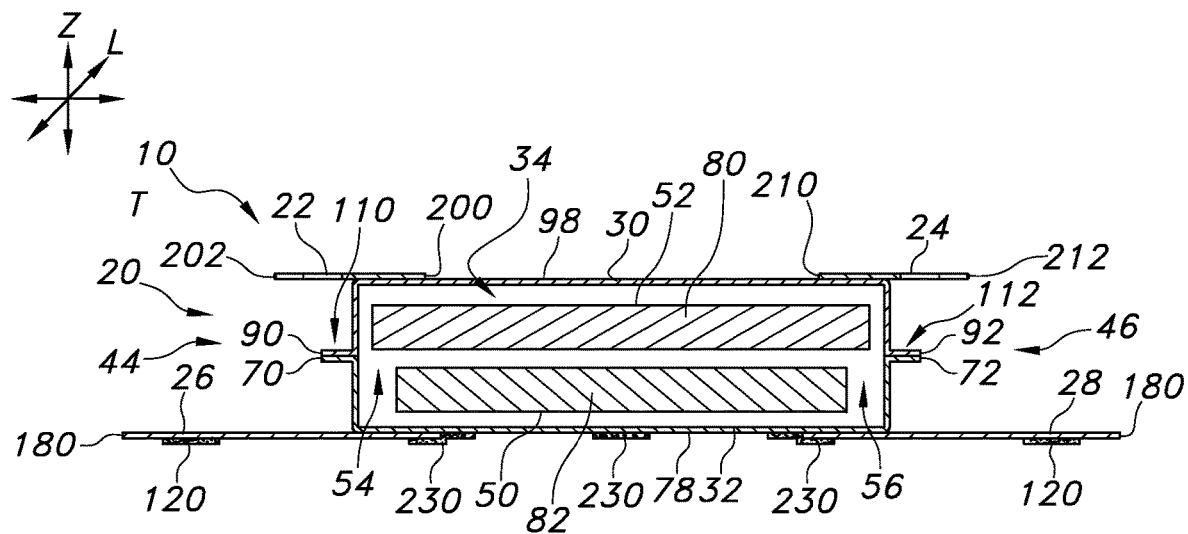
FIG. 7 is an exploded cross-sectional view of the absorbent article of FIG. 5 taken along line 7-7.
Figure 8:
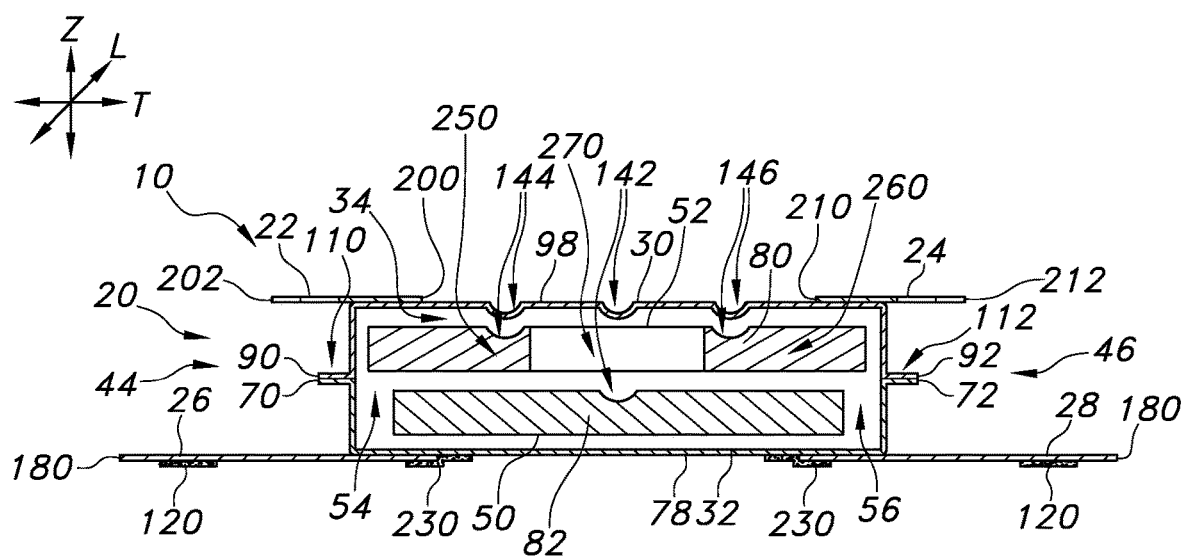
FIG. 8 is an exploded cross-sectional view of the absorbent article of FIG. 5 taken along line 8-8.
Figure 9:
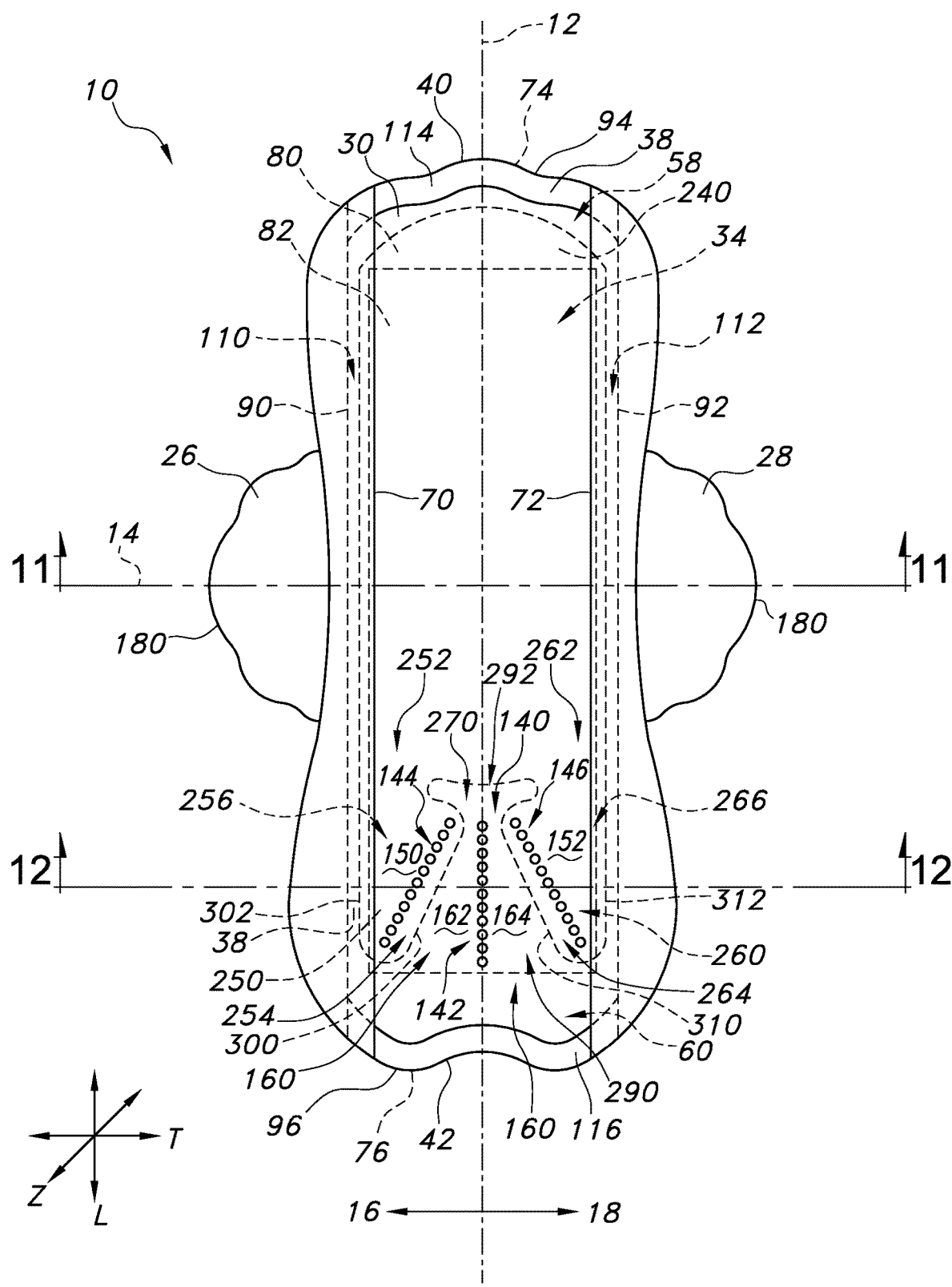
FIG. 9 is a top view of an embodiment of an absorbent article.
Figure 10:
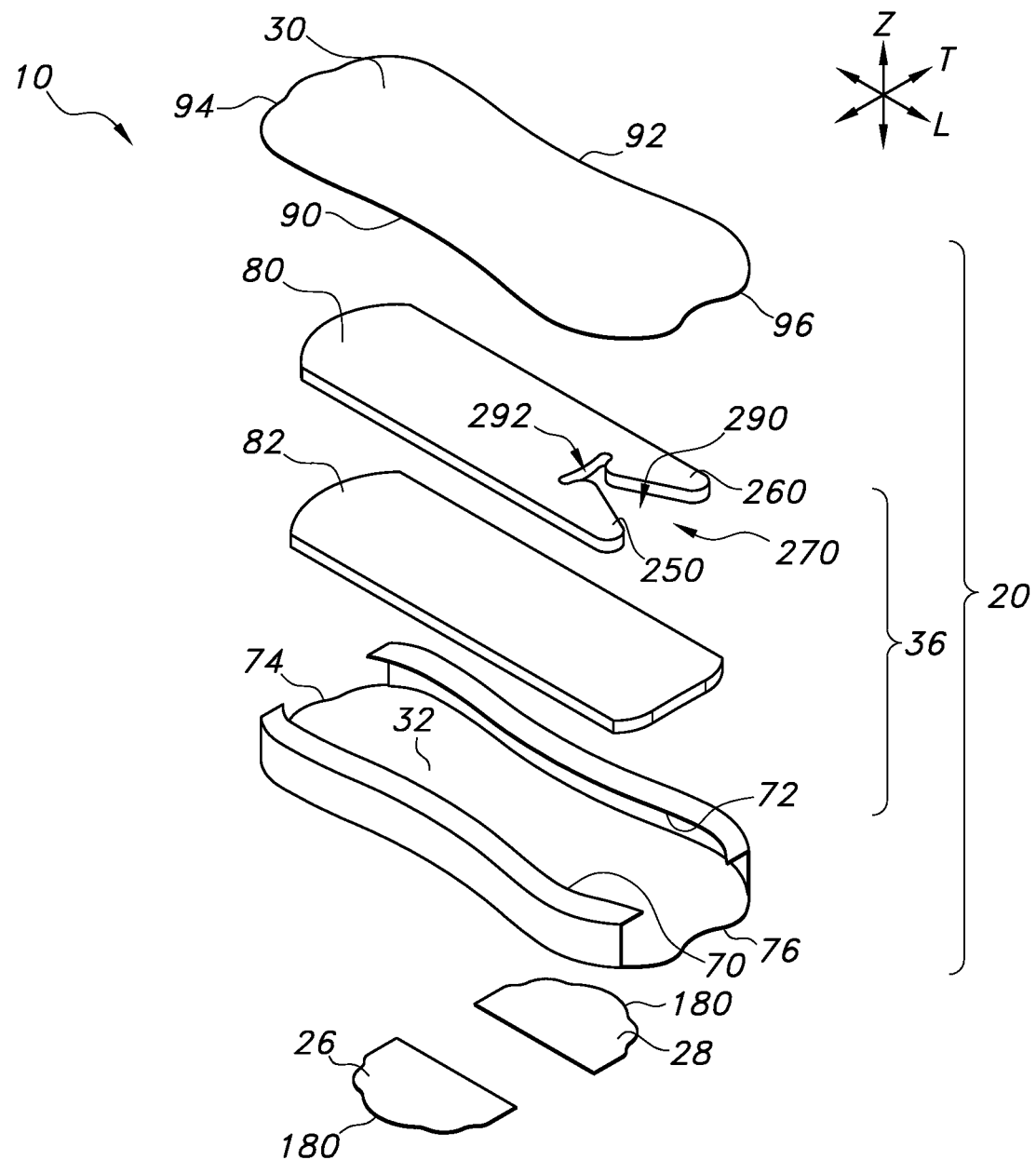
FIG. 10 is an exploded perspective view of the absorbent article of FIG. 9.
Figure 11:
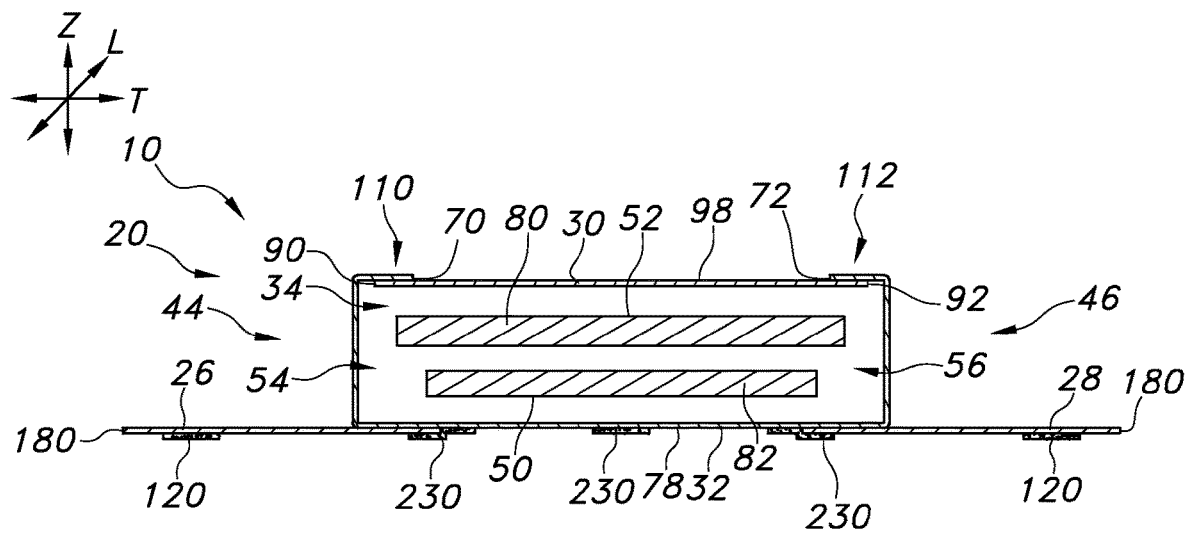
FIG. 11 is an exploded cross-sectional view of the absorbent article of FIG. 9 taken along line 11-11.
Figure 12:
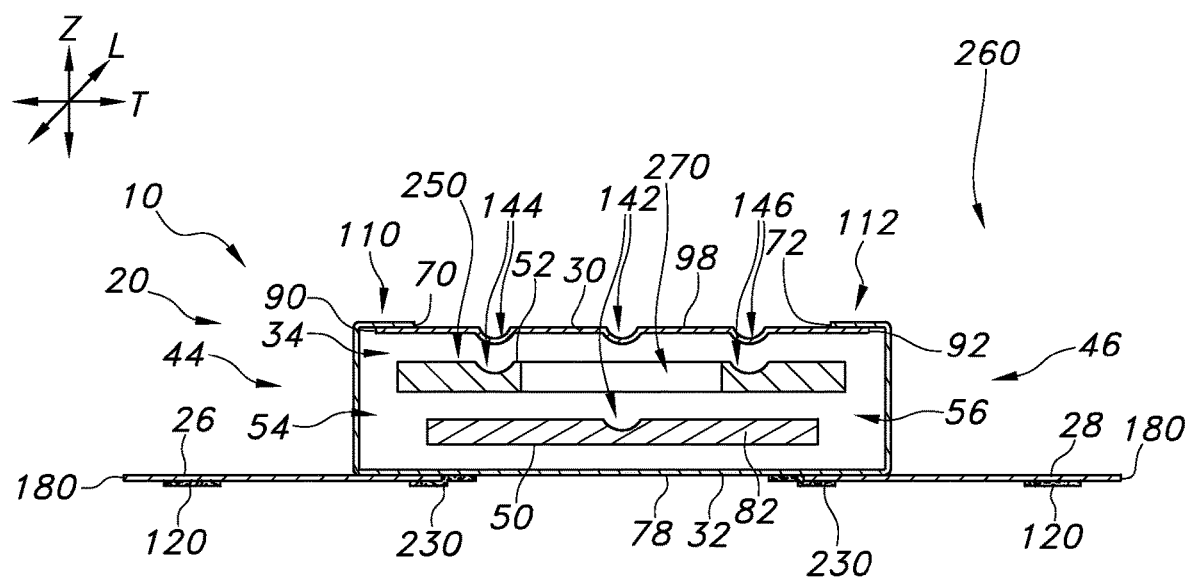
FIG. 12 is an exploded cross-sectional view of the absorbent article of FIG. 9 taken along line 12-12.

Referring to FIGS. 1-4, FIG. 1 provides an illustration of a top view of an embodiment of an exemplary absorbent article 10, FIG. 2 provides an illustration of an exploded perspective view of the absorbent article 10 of FIG. 1, FIG. 3 provides an illustration of a cross-sectional view of the absorbent article 10 of FIG. 1 taken along line 3-3, and FIG. 4 provides an illustration of a cross-sectional view of the absorbent article 10 taken along line 4-4. The absorbent article 10 can have a longitudinal direction (L), a transverse direction (T), and a depth direction (Z). The absorbent article 10 can have a longitudinal axis 12 and a transverse axis 14. The absorbent article 10 can have a chassis 20, an absorbent system 34, and a pair of non-integral wings, 26 and 28. The absorbent article 10 can be symmetrical about the longitudinal axis 12 of the absorbent article 10 and asymmetrical about the transverse axis 14 of the absorbent article 10.

The chassis 20 can have a wearer facing, liquid permeable topsheet layer 30 and a garment facing, liquid impermeable backsheet layer 32. An absorbent system 34 can be positioned between the topsheet layer 30 and the backsheet layer 32 and the absorbent system 34 can have at least an absorbent core 36. In various embodiments, the absorbent core 36 can be formed of two layers, a wearer facing layer 80 and a garment facing layer 82. The topsheet layer 30 and the backsheet layer 32 can be bonded together to form a seal 38 which can contain the absorbent system 34 and body exudates received into the chassis through the topsheet layer 30. The bonding of the topsheet layer 30 and the backsheet layer 32 can be accomplished via any known bonding technique. For example, the topsheet layer 30 and the backsheet layer 32 can be bonded together by adhesive bonding, ultrasonic bonding, thermal bonding, heat press pattern bonding, or any other suitable bonding method known in the art.

The chassis 20 can have a first transverse direction end edge 40, a second transverse direction end edge 42 opposite the first transverse direction end edge 40, and a pair of opposing longitudinal direction side edges, 44 and 46. In various embodiments, the chassis 20 can take on various geometries but will generally have a pair of opposing longitudinal direction side edges, 44 and 46, and a pair of opposing transverse direction end edges 40 and 42. In various embodiments, one or both of the longitudinal direction side edges, 44 and 46, can be linear. In various embodiments, one or both of the longitudinal direction side edges, 44 and 46, can have at least one curve (convex and/or concave) in the longitudinal direction (L) of the chassis 20. In various embodiments, one or both of the transverse direction end edges, 40 and 42, can be linear. In various embodiments, one or both of the transverse direction end edges, 40 and 42, can have at least one curve (convex and/or concave) in the transverse direction (T) of the chassis 20. In various embodiments, one or both of the longitudinal direction side edges, 44 and 46, can be linear in the longitudinal direction (L) of the chassis 20 and one or both of the transverse direction end edges, 40 and 42, can be linear in the transverse direction (T) of the chassis 20. In various embodiments, one or both of the longitudinal direction side edges, 44 and 46, can be linear in the longitudinal direction (L) of the chassis 20 and one or both of the transverse direction end edges, 40 and 42, can have at least one curve (convex and/or concave) in the transverse direction (T) of the chassis 20. In various embodiments, one or both of the longitudinal direction side edges, 44 and 46, can have at least one curve (convex and/or concave) in the longitudinal direction (L) of the chassis 20 and one or both of the transverse direction end edges, 40 and 42, can be linear in the transverse direction (T) of the chassis 20. In various embodiments, one or both of the longitudinal direction side edges, 44 and 46, can have at least one curve (convex and/or concave) in the longitudinal direction (L) of the chassis 20 and one or both of the transverse direction end edges, 40 and 42, can have at least one curve (convex and/or concave) in the transverse direction (T) of the chassis 20. The chassis 20 can be symmetrical about the longitudinal axis 12 of the absorbent article 10 and asymmetrical about the transverse axis 14 of the absorbent article 10.

The absorbent system 34 can have a garment facing surface 50, a wearer facing surface 52, an opposing pair of longitudinal direction peripheral regions, 54 and 56, and an opposing pair of transverse direction peripheral regions, 58 and 60. The garment facing surface 50 of the absorbent system 34 is the surface of the absorbent system 34 which is closest to the undergarment worn by the wearer. The wearer facing surface 52 of the absorbent system 34 is the surface of the absorbent system 34 which is closest to the body of the wearer. The absorbent system 34 can have at least an absorbent core 36 such as illustrated in FIGS. 1-4. The absorbent core 36 can be formed of two layers, a wearer facing layer 80 and a garment facing layer 82. At least one layer of the absorbent system 34, such as, for example, the wearer facing layer 80 of the absorbent core 36, can be a lobed absorbent layer 240 and can have a pair of transversely opposed lobes, 250 and 260, which can define a void space 270 therebetween.

In various embodiments, the absorbent system 34 can have at least one additional layer(s) such as, for example, but not limited to, a surge layer, a fluid intake layer, a transfer delay layer, and/or a distribution layer. It is to be understood that the absorbent system 34 can have any combination of layer(s) deemed suitable. The layer(s) of the absorbent system 34 can be present in any order deemed suitable in the depth direction (Z) of the absorbent article 10 between the topsheet layer 30 and the backsheet layer 32.

In various embodiments, the absorbent article 10 can have at least one flexure feature 140. The at least one flexure feature 140 can be positioned in the chassis 20 in a location intended to be worn towards the posterior of the wearer. The relative position of the at least one flexure feature 140 can be seen in FIGS. 1-4. The at least one flexure feature 140 can help initiate and influence shaping of the absorbent article 10 into a raised and tented configuration. The raised and tented configuration of the absorbent article 10 can conform to the gluteal cleft and can move in response to the alternating movement of the wearer's legs thereby helping the absorbent article 10 stay in place for leakage protection and comfort. In various embodiments, at least a portion of the flexure feature 140 can be associated with the lobed absorbent layer 240 of the absorbent system 34 and the configuration of the lobed absorbent layer 240 and the flexure feature 140 can maintain the absorbent article 10 in the raised and tented configuration when the absorbent article 10 is in use. In various embodiments, at least a portion of the flexure feature 140 can be associated with the void space 270 defined by the lobed absorbent layer 240 of the absorbent system 34. In various embodiments, a portion of the flexure feature 140 can be associated with the void space 270 defined by the lobed absorbent layer 240 of the absorbent system 34 and a portion of the flexure feature 140 can be associated with the lobed absorbent layer 240 of the absorbent system 34.

In various embodiments, such as, for example, illustrated in FIGS. 1-4, the backsheet layer 32 can overlay a garment facing surface 50 of the absorbent system 34 and a portion of each of the longitudinal direction peripheral regions, 54 and 56, of the absorbent system 34. In such embodiments, the topsheet layer 30 can overlay the wearer facing surface 52 of the absorbent system 34 and a portion of each of the longitudinal direction peripheral regions, 54 and 56, of the absorbent system 34. In such embodiments, the longitudinal direction peripheral edges, 90 and 92, of the topsheet layer 30 and the longitudinal direction peripheral edges, 70 and 72, of the backsheet layer 32 can be bonded to each other in the vicinity of the longitudinal direction peripheral regions, 54 and 56, forming longitudinal direction bond regions, 110 and 112. Each of the longitudinal direction bond regions, 110 and 112, form a portion of the seal 38 between the topsheet layer 30 and the backsheet layer 32 of the chassis 20. In such embodiments, the absorbent article 34 can have transverse direction peripheral regions, 58 and 60, beyond which can extend portions of the topsheet layer 30 and the backsheet layer 32. The transverse direction peripheral edges, 94 and 96, of the topsheet layer 30 can be bonded to the transverse direction peripheral edges, 74 and 76, of the backsheet layer 32 to form transverse direction bond regions, 114 and 116, respectively, which can form a portion of the seal 38 between the topsheet layer 30 and the backsheet layer 32 of the chassis 20. In such embodiments, the longitudinal direction bond regions, 110 and 112, and the transverse direction bond regions, 114 and 116, together form the seal 38 of the chassis 20 of the absorbent article 10. In various embodiments, the topsheet layer 30 and the backsheet layer 32 can be sized such that the longitudinal direction peripheral edges, 90 and 92, of the topsheet layer 30 substantially align with the longitudinal direction peripheral edges, 70 and 72, of the backsheet layer 32 in the longitudinal direction bond regions, 110 and 112. In various embodiments, the topsheet layer 30 and the backsheet layer 32 can be sized such that the longitudinal direction peripheral edges, 90 and 92, of the topsheet layer 30 can be positioned closer to the longitudinal axis 12 of the absorbent article 10 than the longitudinal direction peripheral edges, 70 and 72, of the backsheet layer 32 in the longitudinal direction bond regions, 110 and 112. In various embodiments, the topsheet layer 30 and the backsheet layer 32 can be sized such that the longitudinal direction peripheral edges, 90 and 92, of the topsheet layer 30 can be positioned further from the longitudinal axis 12 of the absorbent article 10 than the longitudinal direction peripheral edges, 70 and 72, of the backsheet layer 32 in the longitudinal direction bond regions, 110 and 112.

In various embodiments, such as, for example, illustrated in FIGS. 9-12, the backsheet layer 32 can overlay the garment facing surface 50 of the absorbent system 34, each of the longitudinal direction peripheral regions, 54 and 56, of the absorbent system 34, and a least a portion of the wearer facing surface 52 of the absorbent system 34. In such embodiments, the backsheet layer 32 can partially enclose the absorbent system 34 by wrapping around the absorbent system 34 until the longitudinal direction peripheral edges, 70 and 72, of the backsheet layer 32 overlay a portion of the wearer facing surface 52 of the absorbent system 34. In such embodiments, the portions of the backsheet layer 32 which overlay the longitudinal direction peripheral regions, 54 and 56, can form the longitudinal direction side edges, 44 and 46, of the chassis 20. In such embodiments, the topsheet layer 30 can overlay the wearer facing surface 52 of the absorbent system 34 and can partially enclose the absorbent system 34. In such embodiments, the longitudinal direction peripheral edges, 90 and 92, of the topsheet layer 30 and the longitudinal direction peripheral edges, 70 and 72, of the backsheet layer 32 can be bonded to each other forming longitudinal direction bond regions, 110 and 112. Each of the longitudinal direction bond regions, 110 and 112, overlay the wearer facing surface 52 of the absorbent system 34 and form a portion of the seal 38 between the topsheet layer 30 and the backsheet layer 32 of the chassis 20. In such embodiments, the absorbent system 34 can have transverse direction peripheral regions, 58 and 60, beyond which can extend portions of the topsheet layer 30 and backsheet layer 32. The transverse direction peripheral edges, 94 and 96, of the topsheet layer 30 can be bonded to the transverse direction peripheral edges, 74 and 76, of the backsheet layer 32 to form transverse direction bond regions, 114 and 116, respectively, which can form a portion of the seal 38 between the topsheet layer 30 and the backsheet layer 32 of the chassis 20. In such embodiments, the longitudinal direction bond regions, 110 and 112, and the transverse direction bond regions, 114 and 116, together form the seal 38 of the chassis 20 of the absorbent article 10.

In various embodiments, the topsheet layer 30 can overlay the wearer facing surface 52 of the absorbent system 34, each of the longitudinal direction peripheral regions, 54 and 56, of the absorbent system 34, and at least a portion of the garment facing surface 50 of the absorbent system 34. In such embodiments, the topsheet layer 30 can partially enclose the absorbent system 34 by wrapping around the absorbent system 34 until the longitudinal direction peripheral edges, 90 and 92, of the topsheet layer 30 overlay a portion of the garment facing layer 32 of the absorbent system 34. In such embodiments, the portions of the topsheet layer 30 which overlay the longitudinal direction peripheral regions, 54 and 56, can form the longitudinal direction side edges, 44 and 46, of the chassis 20. In such embodiments, the backsheet layer 32 can overlay the garment facing surface 50 of the absorbent system 34 and can partially enclose the absorbent system 34. In such embodiments, the longitudinal direction peripheral edges, 90 and 92, of the topsheet layer 30 and the longitudinal direction peripheral edges, 70 and 72, of the backsheet layer 32 can be bonded to each other forming longitudinal direction bond regions, 110 and 112. Each of the longitudinal direction bond regions, 110 and 112, overlay the garment facing surface 50 of the absorbent system 34 and form a portion of the seal 38 between the topsheet layer 30 and the backsheet layer 32 of the chassis 20. In such embodiments, the absorbent system 34 can have transverse direction peripheral regions, 58 and 60, beyond which can extend portions of the topsheet layer 30 and backsheet layer 32. The transverse direction peripheral edges, 94 and 96, of the topsheet layer 30 can be bonded to the transverse direction peripheral edges, 74 and 76, of the backsheet layer 32 to form transverse direction bond regions, 114 and 116, respectively, which can form a portion of the seal 38 between the topsheet layer 30 and the backsheet layer 32 of the chassis 20. In such embodiments, the longitudinal direction bond regions, 110 and 112, and the transverse direction bond regions, 114 and 116, together form the seal 38 of the chassis 20 of the absorbent article 10.

In various embodiments, the absorbent article 10 can have a pair of non-integral wings, 26 and 28, extending outwardly, in the transverse direction (T), from the absorbent article 10. The wings, 26 and 28, can be bonded to the exterior surface 78 of the backsheet layer 32 of the chassis 20 of the absorbent article 10. The wings, 26 and 28, can drape over the edges of the wearer's undergarment so that the wings, 26 and 28, are disposed between the edges of the wearer's undergarment and her thighs. The wings, 26 and 28, can serve at least two purposes. First, the wings, 26 and 28, can prevent soiling of the wearer's undergarment by forming a barrier along the edges of the undergarment. Second, each wing, 26 and 28, can be provided with an attachment aid 120, such as, for example, a garment attachment adhesive or a hook, to keep the absorbent article 10 securely and properly positioned in the undergarment. The wings, 26 and 28, can wrap around the crotch region of the wearer's undergarment to aid in securing the absorbent article 10 to the wearer's undergarment when in use. Each wing, 26 and 28, can fold under the crotch region of the wearer's undergarment and the attachment aid 120 can either form a secure attachment to the opposite wing, 26 or 28, or directly to the surface of the wearer's undergarment. In various embodiments, the wings, 26 and 28, can be constructed of materials similar to the topsheet layer 20, the backsheet layer 22 or combinations of these materials. In various embodiments, the wings, 26 and 28, can be separate components which can each individually be bonded to the backsheet layer 32. In various embodiments, the wings, 26 and 28, can be extensions from, and integral with, a wing bridge 190 (shown in FIG. 31) which can be bonded to the backsheet layer 32 and which can extend across the transverse direction (T) width of the absorbent article 10.

In various embodiments, the absorbent article 10 can have a pair of opposing non-integral side covers, 22 and 24. Each of the non-integral side covers, 22 and 24, can extend in the longitudinal direction (L) and can extend the length of the chassis 20 of the absorbent article 10 from the first transverse direction end edge 40 of the chassis 20 to the second transverse direction end edge 42 of the chassis 20. In various embodiments, such as, for example, illustrated in FIGS. 13-16, the non-integral side covers, 22 and 24, can be bonded to an exterior surface 78 of the backsheet layer 32. In such embodiments, the side covers, 22 and 24, can be positioned over the longitudinal direction bond regions, 110 and 112, which form a portion of the seal 38 of the chassis 20 and which are positioned over the wearer facing surface 52 of the absorbent system 34. In such a positioning, the side covers, 22 and 24, can provide a softer and less irritating material to be in contact with the skin of the wearer than the exterior surface 78 of the backsheet layer 32. In such a positioning, the side covers, 22 and 24, can prevent the longitudinal direction bond regions, 110 and 112, from coming into direct contact with the skin of the wearer. In such a positioning, when the wings, 26 and 28, of the absorbent article 10 are wrapped about a wearer's undergarment, the side covers, 22 and 24, which are independent from the wings, 26 and 28, can remain undistorted by the folding of the wings, 26 and 28, about the wearer's undergarment. In various embodiments, such as, for example, illustrated in FIGS. 5-8, the non-integral side covers, 22 and 24, can be bonded to the wearer facing surface 98 of the topsheet layer 30. In such embodiments, the side covers, 22 and 24, can be positioned over the longitudinal direction bond regions, 110 and 112, which form a portion of the seal 38 of the chassis 20 and which are located in the vicinity of the longitudinal direction peripheral regions, 54 and 56. In such a positioning, the side covers, 22 and 24, can provide a softer and less irritating material to be in contact with the skin of the wearer than the seal 38 of the chassis 20. In such a positioning, when the wings, 26 and 28, of the absorbent article 10 are wrapped about a wearer's undergarment, the side covers, 22 and 24, which are independent from the wings, 26 and 28, can remain undistorted by the folding of the wings, 26 and 28, about the wearer's undergarment. In various embodiments, the non-integral side covers, 22 and 24, can be bonded to the wearer facing surface 98 of the topsheet layer 30 in a position overlaying the wearer facing surface 52 of the absorbent system 34 and can be positioned over the longitudinal direction bond regions, 110 and 112, which form a portion of the seal 38 of the chassis 20 and which overlay the garment facing surface 50 of the absorbent system 34. In such a positioning, when the wings, 26 and 28, of the absorbent article 10 are wrapped about a wearer's undergarment, the side covers, 22 and 24, which are independent from the wings, 26 and 28, can remain undistorted by the folding of the wings, 26 and 28, about the wearer's undergarment.

Each of these components of the absorbent article 10, as well as additional components, will be described in more detail herein.

Chassis:

As described herein, the chassis 20 of an absorbent article 10 can have a topsheet layer 30, a backsheet layer 32 and an absorbent system 34 positioned between the topsheet layer 20 and the backsheet layer 32. The absorbent system 34 can have at least one absorbent layer which can be a lobed absorbent layer 240. The absorbent system 34 can have at least an absorbent core 36. The absorbent core 36 can be formed of two layers, a wearer facing layer 80 and a garment facing layer 82. In various embodiments, the absorbent system 34 can have at least one additional layer such as a surge layer 62, a fluid intake layer 64, a transfer delay layer, and/or a distribution layer. The additional layer(s) can be present in any combination deemed suitable. The chassis 20 can further have at least one flexure feature 140 which can be associated with the lobed absorbent layer 240. The configuration of the lobed absorbent layer 240 and the positioning of the flexure feature 140 can provide a flexed, raised and tented configuration to the absorbent article 10 which can be comfortable to wear and which can maintain proper placement for the wearer of the absorbent article 10.

Topsheet Layer:

The topsheet layer 30 defines a wearer facing surface 98 of the absorbent article 10 that may directly contact the body of the wearer and is liquid permeable to receive body exudates. The topsheet layer 30 is desirably provided for comfort and conformability and functions to direct body exudates away from the body of the wearer, through its own structure, and towards the absorbent system 34. The topsheet layer 30 desirably retains little to no liquid in its structure, so that it provides a relatively comfortable and non-irritating surface next to the skin of the wearer of the absorbent article 10.

The topsheet layer 30 can be a single layer of material, or alternatively, can be multiple layers that have been laminated together. The topsheet layer 30 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 30.

In various embodiments, the topsheet layer 30 can be constructed from various nonwoven webs such as melt-blown webs, spunbond webs, hydroentangled spunlace webs, or through air bonded carded webs. Examples of suitable topsheet layer 30 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 30 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 30, each of which is hereby incorporated by reference thereto in its entirety. Additional topsheet layer 30 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 30 may contain a plurality of apertures (not shown) formed therethrough to permit body exudates to pass more readily into the absorbent system 34. The apertures may be randomly or uniformly arranged throughout the topsheet layer 30. The size, shape, diameter, and number of apertures may be varied to suit an absorbent article's 10 particular needs.

In various embodiments, the topsheet layer 30 can have a basis weight ranging from about 5, 10, 15, 20 or 25 gsm to about 50, 100, 120, 125 or 150 gsm. For example, in an embodiment, a topsheet layer 30 can be constructed from a through air bonded carded web having a basis weight ranging from about 15 gsm to about 100 gsm. In another example, a topsheet layer 30 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others.

In various embodiments, the topsheet layer 30 can be at least partially hydrophilic. In various embodiments, a portion of the topsheet layer 30 can be hydrophilic and a portion of the topsheet layer 30 can be hydrophobic. In various embodiments, the portions of the topsheet layer 30 which can be hydrophobic can be either an inherently hydrophobic material or can be a material treated with a hydrophobic coating.

Figure 19:
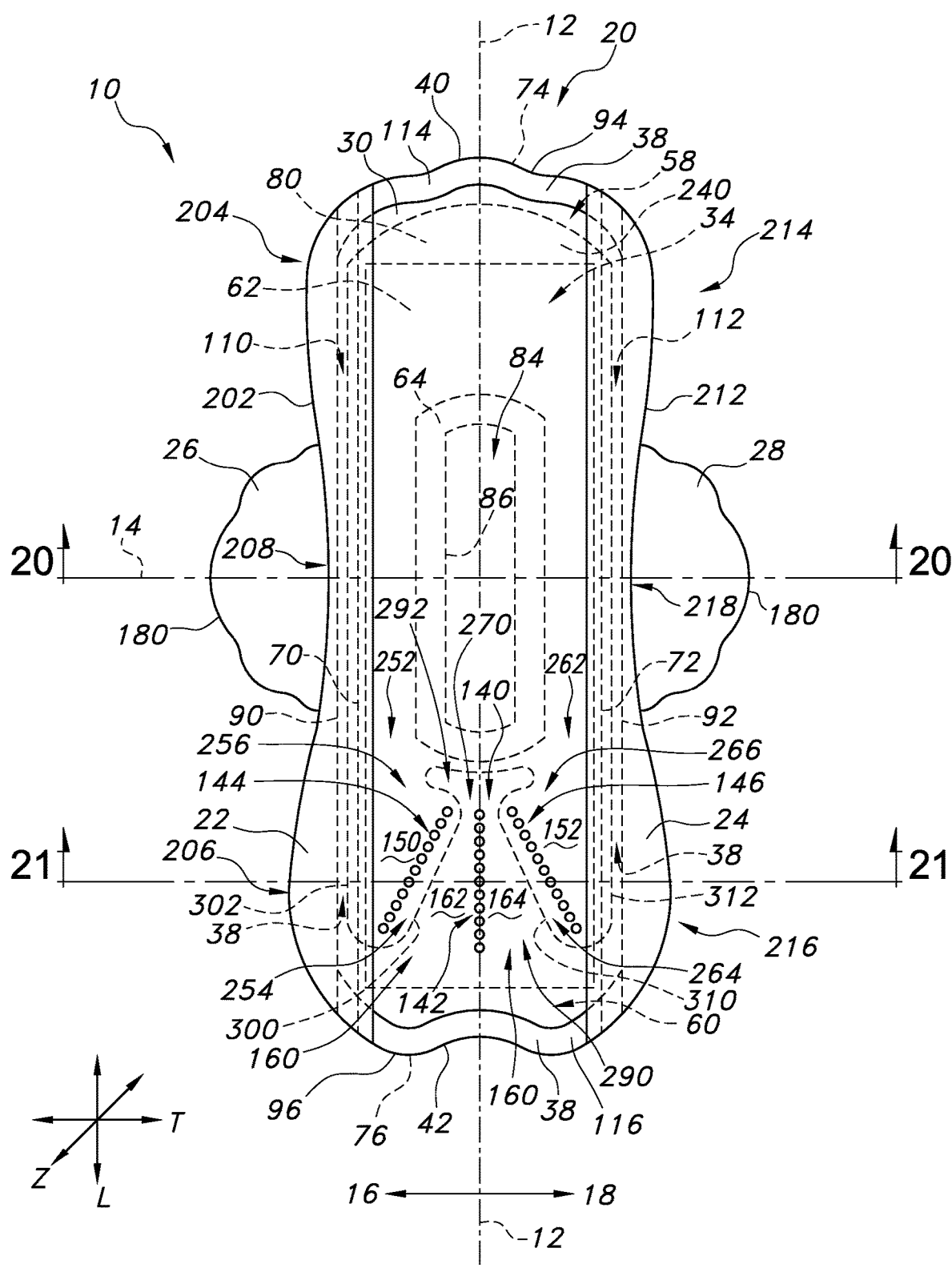
FIG. 19 is a top view of an embodiment of an absorbent article.
Figure 20:
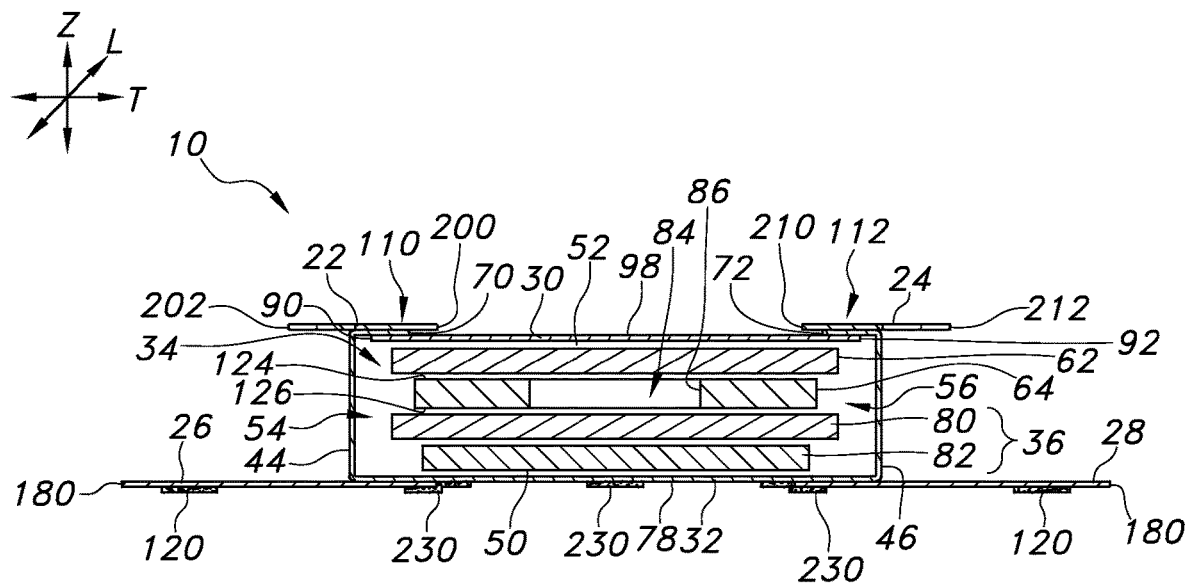
FIG. 20 is an exploded cross-sectional view of the absorbent article of FIG. 19 taken along line 20-20.
Figure 21:
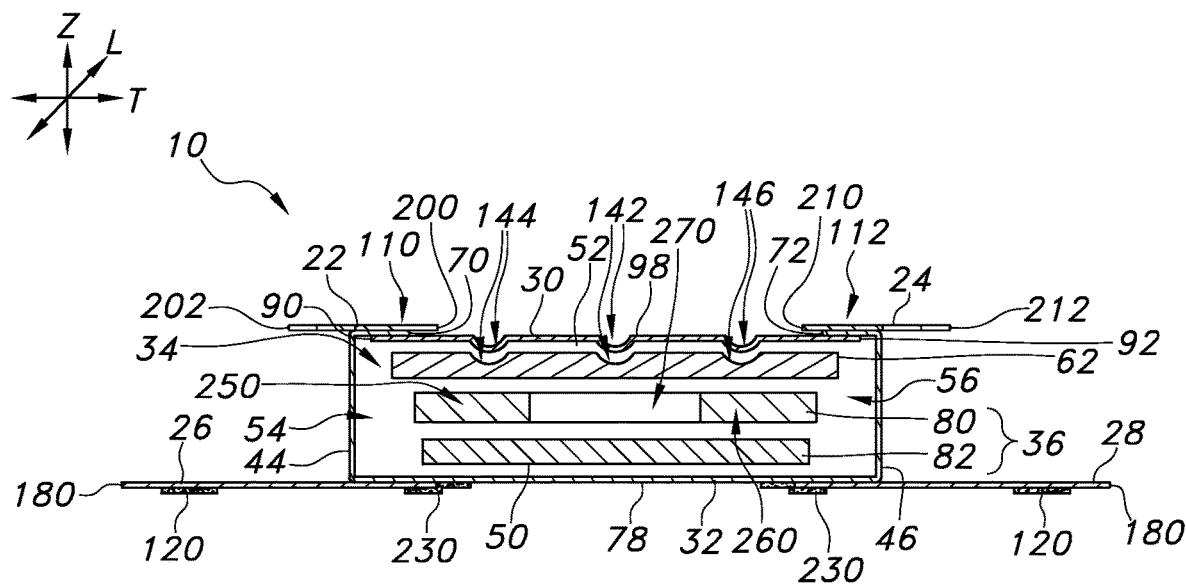
FIG. 21 is an exploded cross-sectional view of the absorbent article of FIG. 19 taken along line 21-21.

Absorbent System:

The absorbent system 34 can have a garment facing surface 50, a wearer facing surface 52, an opposing pair of longitudinal direction peripheral regions, 54 and 56, and an opposing pair of transverse direction peripheral regions, 58 and 60. The garment facing surface 50 of the absorbent system 34 is the surface of the absorbent system 34 which is closest to the undergarment worn by the wearer. The wearer facing surface 52 of the absorbent system 34 is the surface of the absorbent system 34 which is closest to the body of the wearer. The absorbent system 34 can have at least an absorbent core 36 such as illustrated in FIGS. 1-4. In various embodiments, the absorbent core 36 can be a single layer construction. In various embodiments, the absorbent core 36 can have at least two layers of material, such as a wearer facing layer 80 and a garment facing layer 82 such as illustrated in FIGS. 1-4. In various embodiments, the absorbent system 34 can have additional layers such as, for example, but not limited to, a surge layer, a fluid intake layer, a transfer delay layer, and/or a distribution layer. FIGS. 19-21 illustrate an embodiment of an absorbent article 10 having an absorbent system 34 which can have an absorbent core 36 having two layers of material, 80 and 82, a surge layer 62 and a fluid intake layer 64. It is to be understood that the absorbent system 34 can have any combination of layer(s) (e.g., a surge layer, a fluid intake layer, a transfer delay layer, an absorbent core, and/or a distribution layer) as well any additional layer deemed suitable. The layer(s) of the absorbent system 34 can be present in any order deemed suitable in the depth direction (Z) of the absorbent article 10 between the topsheet layer 30 and the backsheet layer 32. At least one layer of the absorbent system 34 can be a lobed absorbent layer 240.

In an embodiment, the absorbent system 34 can have an absorbent core 36 which can be a single layer construction. In an embodiment, the absorbent system 34 can have an absorbent core 36 which can be a single layer construction and the absorbent system 34 can have at least one, two, three or four additional layer(s) which can be selected from a surge layer 62, a fluid intake layer 64, a transfer delay layer, and/or a distribution layer. In an embodiment, the absorbent system 32 can have an absorbent core 36 which can be of a two layer construction, such as having a wearer facing layer 80 and a garment facing layer 82. In an embodiment, the absorbent system 34 can have an absorbent core 36 which can have at least two layers of material, such as a wearer facing layer 80 and a garment facing layer 82, and the absorbent system 34 can have at least one, two, three, or four additional layer(s) which can be selected from a surge layer 62, a fluid intake layer 64, a transfer delayer layer, and/or a distribution layer.

Absorbent Core:

The absorbent system 34 can have an absorbent core 36 positioned between the topsheet layer 30 and the backsheet layer 32, such as illustrated in FIGS. 1-4. The absorbent core 36 can generally be any single layer structure or combination of layer components, which can demonstrate some level of compressibility, conformability, be non-irritating to a wearer's skin, and capable of absorbing and retaining liquids and other body exudates. Additionally, the absorbent core 36 can provide additional capacity to absorb and retain body exudates such as menses. In various embodiments, the absorbent core 36 can be formed from a variety of different materials and can contain any number of desired layers. For example, the absorbent core 36 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 36 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 36 in any amount as desired.

Regardless of the combination of absorbent materials used in the absorbent core 36, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 36 can vary as desired and can comprise any one of various shapes including, but not limited to, triangular, rectangular, dog-bone and elliptical shapes. In various embodiments, the absorbent core 36 can have a shape that generally corresponds with the overall shape of the chassis 20. The dimensions of the absorbent core 36 can be substantially similar to those of the chassis 20, however, it will be appreciated that the dimensions of the absorbent core 36 while similar, will often be less than those of the overall chassis 20, in order to be adequately contained therein.

By way of example, suitable materials and/or structures for the absorbent core 36 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

As described above, in various embodiments, an absorbent core 36 can be a single layer structure and can include, for example, a matrix of cellulosic fluff and superabsorbent material. In various embodiments, an absorbent core 36 can have at least two layers of material, such as, for example, a wearer facing layer 80 and a garment facing layer 82, such as illustrated in FIGS. 1-4. In various embodiments, the two layers, 80 and 82, can be identical to each other. In various embodiments, the two layers, 80 and 82, can be different from each other. In such embodiments, the two layers, 80 and 82, can provide the chassis 20 with different absorption properties as deemed suitable. In various embodiments, the wearer facing layer 80 of the absorbent core 36 may be constructed of an airlaid material and the garment facing layer 82 of the absorbent core 36 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

In various embodiments, such as illustrated in FIGS. 1-4, the absorbent article 10 can have an absorbent system 34 which can have at least two layers. In such embodiments, at least one of the layers of the absorbent system 34 can be a lobed absorbent layer 240. In the embodiments illustrated in FIGS. 1-4, the two layers of the absorbent system 34 are a wearer facing layer 80 and a garment facing layer 82 of an absorbent core 36 wherein the wearer facing layer 80 of the absorbent core 36 is a lobed absorbent layer 240. In various embodiments in which the absorbent system 34 has a single layer absorbent core 36, the absorbent system 34 can have a second layer of material, such as, for example, a surge layer 62, a fluid intake layer 64, a transfer delay layer and/or a distribution layer and at least one of the layers of the absorbent system 34 can be a lobed absorbent layer 240. Further details regarding a lobed absorbent layer 240 will be provided later herein.

Additional Absorbent System Layers:

As described herein, the absorbent system 34 can have at least an absorbent core 36 and, in various embodiments, the absorbent system 34 can have at least one additional layer. The at least one additional layer can be at least one of a surge layer 62, a fluid intake layer 64, a transfer delay layer, and/or a distribution layer. FIGS. 19-21 provide an exemplary illustration of an absorbent system 34 which has a surge layer 62, a fluid intake layer 64, and an absorbent core 36 which has a wearer facing layer 80 and a garment facing layer 82. The absorbent article 10 illustrated in the Figures is non-limiting and additional arrangements of layer(s) in the absorbent system 34 are contemplated herein.

Surge Layer:

In various embodiments, an absorbent system 34 can include a surge layer 62 positioned between the topsheet layer 30 and the absorbent core 36. A surge layer 62 can be constructed of any woven or nonwoven material that is easily penetrated by body exudates. The surge layer 62 can help to absorb, decelerate, and diffuse surges or gushes of liquid that may be rapidly introduced into the chassis 20. The surge layer 62 can rapidly accept and temporarily hold the liquid prior to releasing the liquid into, for instance, the absorbent core 36 or any other layer of the absorbent system 34. Various woven fabrics and nonwoven webs can be used to construct the surge layer 62. For example, the surge layer 62 can comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layer 62 can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The surge layer 62 can typically have a basis weight of less than about 100 gsm, and in some embodiments, from about 10 gsm to about 40 gsm.

Fluid Intake Layer:

In various embodiments, the absorbent system 34 can include a liquid permeable fluid intake layer 64. Such a fluid intake layer 64 can be made of a material that can be capable of rapidly transferring, in the Z-direction, body exudates that are delivered to the topsheet layer 30. The fluid intake layer 64 can generally have any shape and/or size desired. In an embodiment, the fluid intake layer 64 can have a curved rectangular shape, with a length equal to or less than the overall length of the chassis 20, and a width less than the width of the chassis 20. For example, the fluid intake layer 64 can have a length of between about 20, 40 or 60 mm to about 150, 150, 175, 200 or 300 mm and a width of between about 10, 15 or 20 mm to about 60, 80 or 100 mm may be utilized. The fluid intake layer 64 can have a thickness in the depth direction (Z) from about 0.5 mm to about 3 mm. Any of a variety of different materials can be capable of being used for the fluid intake layer 64 to accomplish the above-mentioned functions. The material may be synthetic, cellulosic, or a combination of synthetic and cellulosic materials. The fluid intake layer 64 can be constructed from any woven or nonwoven material. For example, the fluid intake layer 64 can be constructed as an airlaid or TABCW material.

For example, airlaid cellulosic tissues may be suitable for use in the fluid intake layer 64. The airlaid cellulosic tissue may have a basis weight ranging from about 10 or 100 gsm to about 250 or 300 gsm. The airlaid cellulosic tissue can be formed from hardwood and/or softwood fibers. An airlaid cellulosic tissue can have a fine pore structure and can provide an excellent wicking capacity, especially for menses.

Additionally, to further enhance the ability of the chassis 20 to transfer body exudates in the depth direction (Z) from the topsheet layer 30 toward any lower layers in the chassis 20 as well as to enhance the ability of the fluid intake layer 64 to conform to the wearer's body based on its ability to bend, the fluid intake layer 64 can have an opening 84 (shown in FIGS. 19-21) in the fluid intake layer 64 which can be any suitable shape, such as ovular, circular, rectangular, square, triangular, etc. In various embodiments, the opening 84 in the fluid intake layer 64 can be elongate and can be oriented in the longitudinal direction of the chassis 20. The opening 84 in the fluid intake layer 64 can be bounded by a perimeter 86 which can form an inner border or inner edge of the fluid intake layer 64. The opening 84 can extend in the depth direction (Z) of the fluid intake layer 64 from an upper, wearer facing surface 124 of the fluid intake layer 64 through and to a lower, garment facing surface 126 of the fluid intake layer 64.

The opening 84 can be located at various positions along the longitudinal and transverse axes of the fluid intake layer 64 depending upon the primary location of body exudate intake or the purpose for which the absorbent article 10 is being used. For example, in various embodiments, the fluid intake layer 64 and the opening 84 in the fluid intake layer 64 can be positioned so that it is in substantial alignment with the longitudinal axis 12 and the transverse axis 14 of the absorbent article 10. This allows the opening 84 to be centrally disposed so that it can be positioned below the main point of body exudate discharge and so that it can act as the primary body exudate receiving area for the absorbent article 10.

However, centralized positioning of the fluid intake layer 64 and the opening 84 of the fluid intake layer 64 is not required, and in various embodiments, depending on the primary location where body exudate intake might occur, the fluid intake layer 64 and the opening 84 of the fluid intake layer 64 may be substantially aligned with the longitudinal axis 12 only. Thus, in various embodiments, the fluid intake layer 64 and the opening 84 of the fluid intake layer 64 may be shifted in the longitudinal direction towards either transverse direction end edge, 40 or 42, of the chassis 20, so that the opening 84 of the fluid intake layer 64 is not in substantial alignment with the transverse axis 14 of the absorbent article 10.

The opening 84 in the fluid intake layer 64 can have a longitudinal length from about 15, 20, 30 or 50 mm to about 60, 75, 100 or 150 mm and can have a transverse width from about 10, 15, 20 or 30 mm to about 40, 60 or 80 mm. The opening 84 in the fluid intake layer 64 can be defined by the perimeter 86 and can have a length that is from about 15, 20 or 25% to about 70, 75, or 80% of the overall longitudinal length of the fluid intake layer 64 in the longitudinal direction. The opening 84 in the fluid intake layer 64 can be defined by the perimeter 86 and can have a width that can be from about 20, 25 or 30% to about 70, 75 or 80% of the overall width of the fluid intake layer 64 in the transverse direction. The opening 84 in the fluid intake layer 64 can serve to funnel and direct body exudates from the topsheet layer 30 and towards lower layers of the chassis 20 in the depth direction (Z). The opening 84 in the fluid intake layer 64 can also form a cup or well-like structure for holding body exudates and preventing leakage away from a central region of the absorbent article 10 and towards the edges of the absorbent article 10.

Transfer Delay Layer:

In various embodiments, an absorbent system 34 can include a liquid permeable transfer delay layer (not shown) positioned between the topsheet layer 30 and the absorbent core 36. The transfer delay layer may contain a material that is substantially hydrophobic. For example, the transfer delay layer may be a nonwoven fibrous web composed of relatively hydrophobic materials, such as polypropylene, polyethylene, polyester, or the like, and also may be composed of a blend of such materials. One example of a material suitable for the transfer delay layer can be a spunbond web composed of polypropylene, multi-lobal fibers. Further examples of suitable transfer delay layers can include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al., each of which is incorporated herein by reference.

The transfer delay layer may generally have any size, such as a length of about 150 mm to about 300 mm. Typically, the length of the transfer delay layer can be approximately equal to the length of the chassis 20. The width of the transfer delay layer can be from between about 50 mm to about 75 mm. The transfer delay layer can have a basis weight less than about 250 gsm, and in some embodiments, between about 40 gsm and about 200 gsm.

Distribution Layer:

In various embodiments, the absorbent system 34 can have a distribution layer (not shown) positioned below the absorbent core 36 and between the absorbent core 36 and the backsheet layer 32. The distribution layer can increase absorbency of the chassis 20. The distribution layer can be constructed of various materials such as, but not limited to, hydroentangled webs, through air bonded carded webs, meltblown webs, and meltblown microfiber webs. The distribution layer can include a hydrophilic material. The distribution layer can be smaller in size than the absorbent core 36.

In various embodiments, the distribution layer can have a longitudinal length from about 80, 90, 100, 110, 120, 125 or 130 mm to about 135, 140, 150, 160, 170, 180 or 190 mm and can have a transverse width from about 30, 35 or 40 mm to about 45, 50, 55 or 60 mm. In various embodiments, the distribution layer can have a density of greater than about 0.1 grams per cubic centimeter. The density can be calculated utilizing the formula: density=basis weight (gsm)/thickness (mm)/1000. In various embodiments, the distribution layer can have a basis weight from about 10, 20, 25, 30 or 50 gsm to about 60, 70, 80, 90, 100, 120, 140, 150, 160, 180 or 200 gsm.

In various embodiments, the distribution layer can be a hydroentangled web. The hydroentangled web can include a hydroentangled spunbond material and a pulp material. The hydroentangled spunbond material can include a polypropylene material. The spunbond material can be present in an amount from about 10% or 15% to about 20% or 25% of the hydroentangled web. The pulp material can be present in an amount from about 75% or 80% to about 85% or 90% of the hydroentangled web. The hydroentangled web can have a basis weight from about 30 or 60 gsm to about 90 or 200 gsm. The basis weight of the hydroentangled web can be balanced with the desired flexibility of the absorbent article 10. In various embodiments, the distribution layer can include a bicomponent fluid distribution layer, which can increase absorbency by providing a high void space and may be made of a through air bonded carded web, having a basis weight, in an embodiment, of between about 25 gsm and 100 gsm. In various embodiments, the distribution layer can be a meltblown microfiber web of polypropylene material and can have a basis weight from about 10 or 20 gsm to about 30, 50 or 100 gsm. In various embodiments, the meltblown microfiber web can be treated with wetting agents for adequate handling of body exudates. Examples of wetting agents can include, but are not limited to, surface active agents (or surfactants) having a hydrophilic lipophilic balance (HLB) of at least 6, 7 or 18. A variety of surfactants can be used and can include, but are not limited to, anionic, cationic, or neutral from a charge standpoint. Mixtures of surfactants and other wetting agents can also be used. A wetting agent add-on can range from about 0.1 or 0.2% to about 5 or 10%. In various embodiments, an add-on amount can be higher than 10%. For example, the meltblown microfiber web can be treated to impart hydrophilicity by either Aerosol GPG of Cytec or Ahcovel Base N-62 for example. Such material is available from Yuhan-Kimberly Ltd., Seoul, Korea and FiberTex, Malaysia.

Lobed Absorbent Layer:

As illustrated in the Figures, at least one layer of the absorbent system 34 can be a lobed absorbent layer 240 such as, for example, a wearer facing layer 80 of a dual layer absorbent core 36. The configuration of the lobed absorbent layer 240 can provide a flexed, raised and tented configuration to the absorbent article 10 which can be comfortable to wear and which can maintain proper placement for the wearer of the absorbent article 10.

Figure 17A:
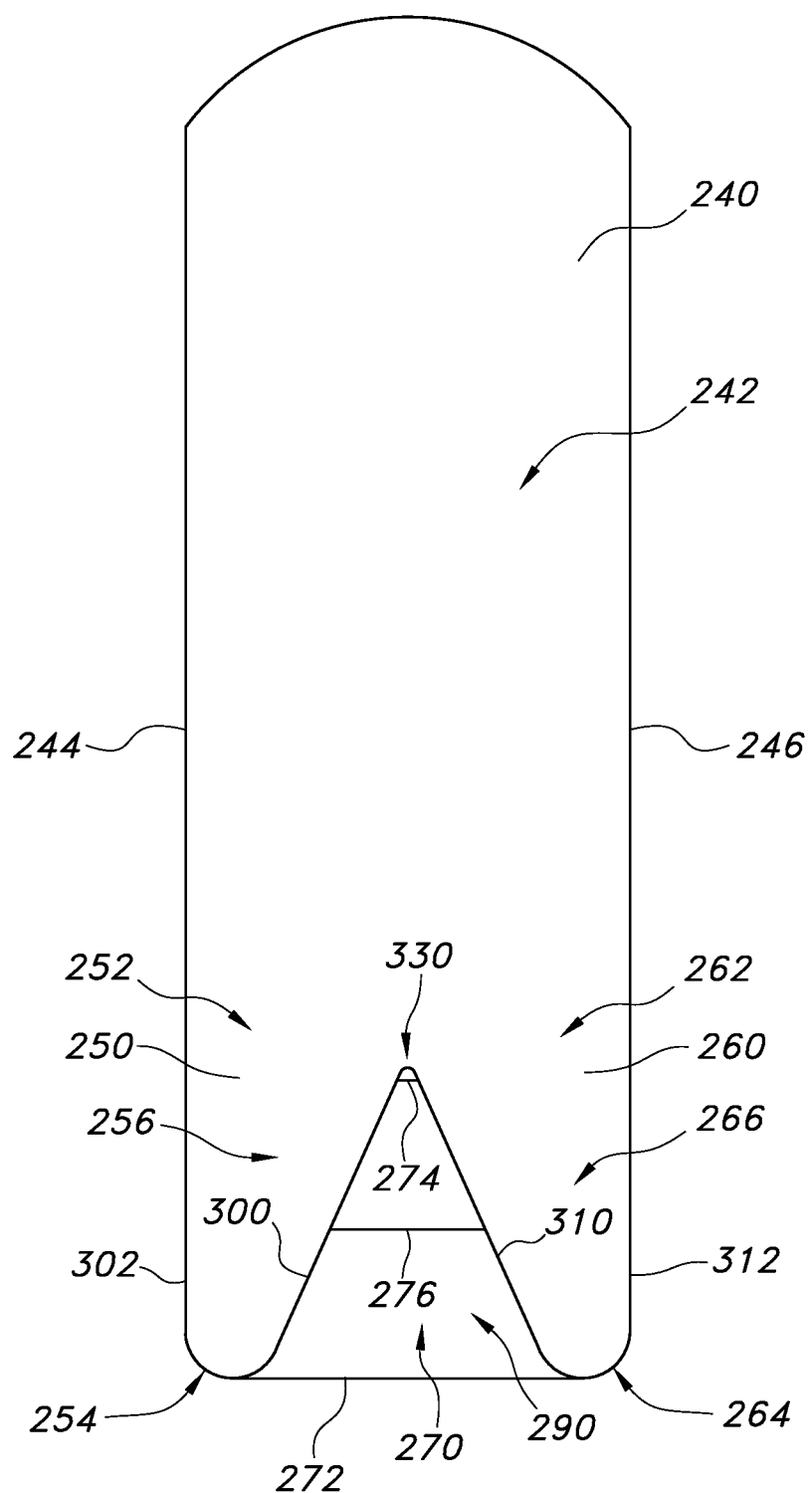
FIGS. 17A and 17B are top views of a lobed absorbent layer of an absorbent system.
Figure 17B:
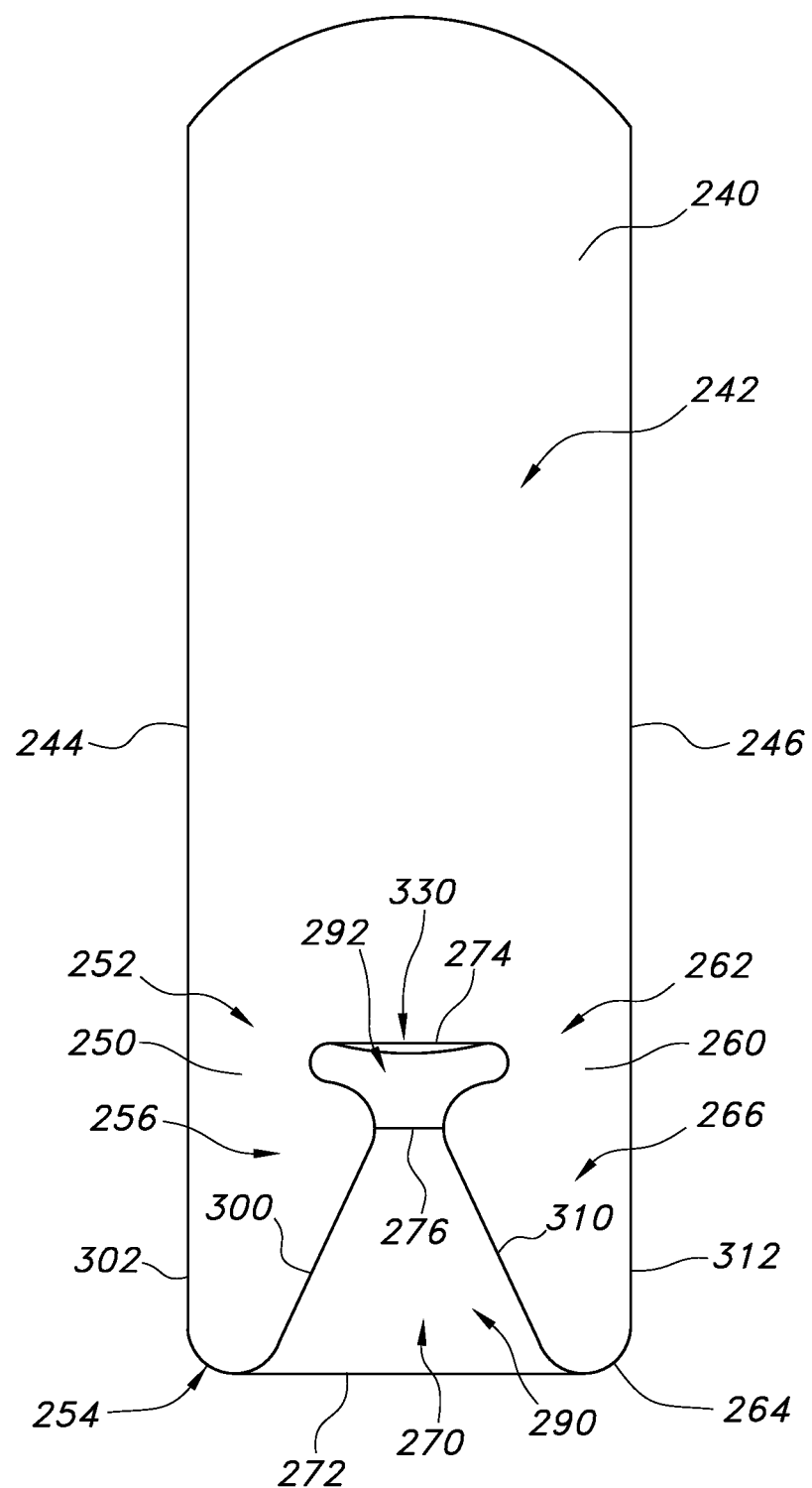

As illustrated in FIGS. 17A and 17B, the lobed absorbent layer 240 can have a pair of opposing lobes, 250 and 260, and the lobed absorbent layer 240 of the absorbent system 34 can be positioned in an absorbent article 10 such that the lobes, 250 and 260, can be in the anterior region of the absorbent article 10 or in the posterior region of the absorbent article 10. In various embodiments, the lobed absorbent layer 240 can have multiple pairs of opposing lobes, 250 and 260. In various embodiments, such as, for example, when the lobed absorbent layer 240 has at least two pairs of opposing lobes, 250 and 260, one of the pairs of opposing lobes, 250 and 260, can be positioned in the anterior region of the absorbent article 10 and the other of the pair of opposing lobes, 250 and 260, can be positioned in the posterior region of the absorbent article 10.

In various embodiments, each lobe, 250 or 260, in a pair of opposing lobes, 250 and 260, can extend in a longitudinal direction (L) and can extend longitudinally in a direction away from the transverse axis 14 of the absorbent article 10. Each of the lobes, 250 and 260, can have a proximal end, 252 and 262, respectively, located closer to the transverse axis 14 of the absorbent article 10 than a distal end, 254 and 264, respectively, of each of the lobes, 250 and 260, respectively. The distal ends, 254 and 264, respectively, can be positioned closer to a transverse direction end edge(s), 40 and/or 42, of the absorbent article 10. The proximal ends, 252 and 262, and the distal ends, 254 and 264, can be separated by a mid-section, 256 and 266, respectively.

In various embodiments, the lobes, 250 and 260, can be configured in any shape deemed suitable to provide the desired raised and tented configuration when the absorbent article 10 is in use. Each lobe, 250 and 260, can have an interior edge, 300 and 310, respectively, and an exterior edge, 302 and 312, respectively. Each of the exterior edges, 302 and 312, can form a portion of a longitudinal direction side edge, 244 and 246, respectively, of the lobed absorbent layer 240. Each of the interior edges, 300 and 310, can extend from a distal end, 254 and 264, respectively, of each of the lobes, 250 and 260, respectively, and in a direction towards an interior region 242 of the lobed absorbent layer 240 where they can join together at a terminus 330 in the vicinity of the proximal ends, 252 and 262, respectively, of the lobes, 250 and 260, respectively.

The interior edges, 300 and 310, of each of the lobes, 250 and 260, respectively, can, at least partially, define a void space 270 in the lobed absorbent layer 240 and can, therefore, at least partially provide a perimeter to the void space 270. In various embodiments, the interior edges, 300 and 310, can provide a perimeter to about least about 40% of the void space 270 of a lobed absorbent layer 240. In various embodiments, the interior edges, 300 and 310, can provide from about 40, 45, 50, 55, 60 or 65% to about 70, 75, 80, 85, 90, 95 or 100% of a perimeter to a void space 270 in a lobed absorbent layer 240. In various embodiments, the formation of the void space 270 can be due to the removal of material from the absorbent layer of the absorbent system 34 chosen to be the lobed absorbent layer 240. The void space 270 can also be formed during the formation of the lobes, 250 and 260, from separate pieces of material that can then be joined together, typically in an area adjacent the longitudinal axis 12 of the absorbent article 10. Alternatively, the void space 270 and the lobes, 250 and 260, can be formed as a result of the formation of the lobed absorbent layer 240 being formed in a mold having the desired end shape as when using pockets in a forming drum in connection with fibrous structures or a shaped mold when using foam materials.

In various embodiments, the interior edges, 300 and 310, of each of the lobes, 250 and 260, respectively, can be configured in any shape as deemed suitable to provide the desired configuration of the lobes, 250 and 260, respectively. In various embodiments, the interior edges, 300 and 310, of each of the lobes, 250 and 260, respectively, can each have a portion which can be linear, arcuate, or combinations thereof. In various embodiments, the interior edges, 300 and 310, of each of the lobes, 250 and 260, respectively, can have a portion which can be linear and can have a portion which can be arcuate.

As the exemplary and non-limiting illustrations of FIGS. 17A, 17B and 18A-18D illustrate, the design of the lobes, 250 and 260, can take any shape as deemed suitable. The distal ends, 254 and 264, of the lobes, 250 and 260, respectively, can be separated from each other in the transverse direction (T) by a distal distance 272. The mid-sections, 256 and 266, of the lobes, 250 and 260, respectively, can be separated from each other in the transverse direction (T) by a mid-distance 276. The proximal ends, 252 and 262, of the lobes, 250 and 260, respectively, can be separated from each other in the transverse direction (T) by a proximal distance 274. In various embodiments, the distal distance 272 can be greater than the mid-distance 276 and the mid-distance 276 can be greater than the proximal distance 274. In various embodiments, the distal distance 272 can be greater than the mid-distance 276 and the mid-distance 276 can be less than the proximal distance 274. In various embodiments, the distal distance 272 can be less than the mid-distance 276 and the mid-distance 276 can be greater than the proximal distance 274. In various embodiments, the distal distance 272 can be less than the mid-distance 276 and the mid-distance 276 can be less than the proximal distance 274.

In various embodiments, the void space 270 can be centered on the longitudinal axis 12 of the absorbent article 10 and the void space 270 can have a portion which can be a generally longitudinally extending void space 290, such as, for example, illustrated in FIG. 17A. A generally longitudinally extending void space 290 can have a principal bending axis generally parallel to the longitudinal axis 12 of the absorbent article 10 when the absorbent article 10 is in use. The length in the longitudinal direction (L) of the longitudinally extending void space 290 can be any length as deemed suitable. In various embodiments, the distal distance 272 can be greater than the mid-distance 276 and the mid-distance 276 can be greater than the proximal distance 274. In various embodiments, the distal distance 272 can be less than the mid-distance 276 and the mid-distance 276 can be less than the proximal distance 274. In various embodiments, such as illustrated in FIG. 17A, the interior edges, 300 and 310, can diverge from the terminus 330 to the distal ends, 254 and 264, respectively, of the lobes, 250 and 260, respectively, at an angle relative to the longitudinal axis 12 of the lobed absorbent layer 240 which can be from about 1, 2, 3, 5, 7 or 10 degrees to about 15, 20, 25, 30, 35, 40 or 45 degrees. In such embodiments, the lobed absorbent layer 240 can have a generally V-shaped void space 270 defined by and positioned between the lobes, 250 and 260, of the lobed absorbent layer 240. In such embodiments, the distal distance 272 can be greater than the mid-distance 276 and the mid-distance 276 can be greater than the proximal distance 274.

In various embodiments, the void space 270 can be centered on the longitudinal axis 12 of the absorbent article 10 and the void space 270 can have a portion which can be a generally longitudinally extending void space 290 and can have a portion which can be a generally transversely extending void space 292, such as, for example, illustrated in FIG. 17B. A generally transversely extending void space 292 can have a principal bending axis generally parallel to the transverse axis 14 of the absorbent article 10 when the absorbent article 10 is in use. In various embodiments, the longitudinal extending void space 290 can connect to the transverse extending void space 292. In various embodiments, the longitudinal extending void space 290 can be separate and distinct from the transverse extending void space 292. The length in the longitudinal direction (L) of the longitudinally extending void space 290 can be any length as deemed suitable and the width in the transverse direction (T) of the transversely extending void space 292 can be any width as deemed suitable. In various embodiments, the distal distance 272 can be greater than the mid-distance 276 and the mid-distance 276 can be less than the proximal distance 274. In such embodiments, the proximal distance 274 can be from about 10 or 15 mm to about 30 or 40 mm, the mid-distance 276 can be from about 1 or 3 mm to about 15 or 30 mm, and the distal distance 272 can be from about 30 or 40 mm to about 60 or 70 mm. In various embodiments, such as illustrated in FIG. 17B, the interior edges, 300 and 310, can diverge from the terminus 330 to the distal ends, 254 and 264, respectively, of the lobes, 250 and 260, respectively, and can be provided with a shaped configuration such that the resultant void space 270 can be a shape other than the V-shaped void space 270 as illustrated in FIG. 17A. In such embodiments, the distal distance 272 can be greater than the mid-distance 276 and the mid-distance 276 can be less than the proximal distance 274.

Figure 18A:
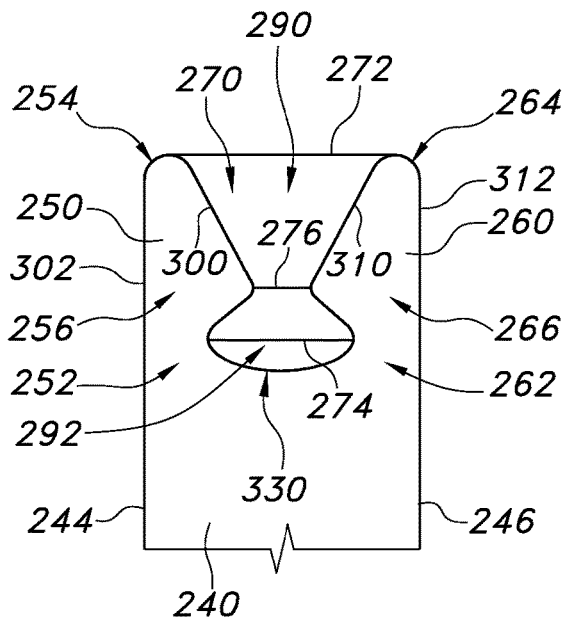
FIGS. 18A-18D are partial top views of alternate lobed absorbent layers of an absorbent system.
Figure 18B:
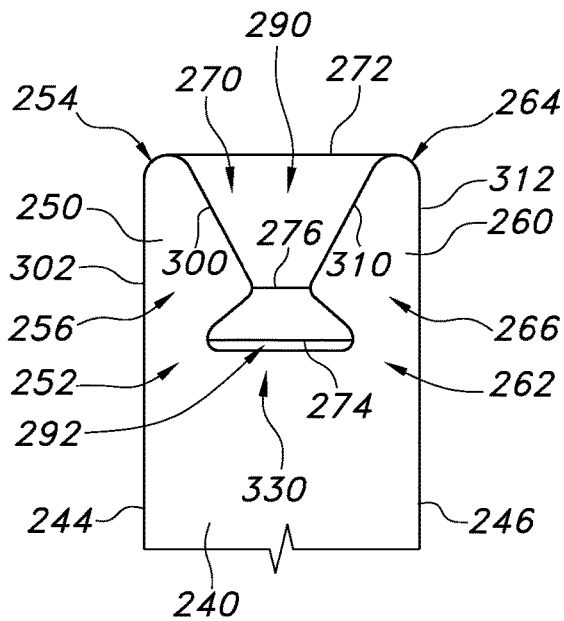
Figure 18C:
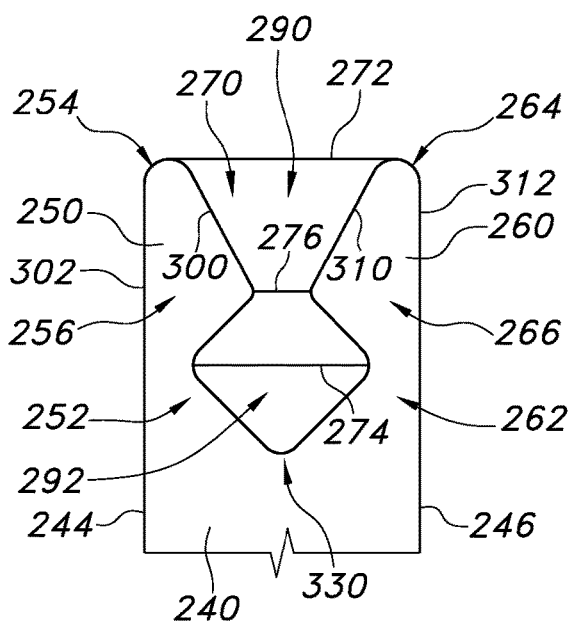
Figure 18D:
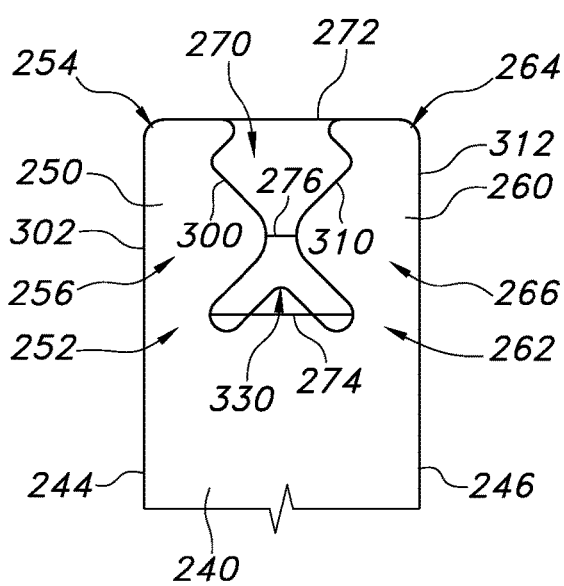

FIGS. 18A-18D provide additional exemplary illustrations in which the distal distance 272 can be greater than the mid-distance 276 and the mid-distance can be less than the proximal distance 274. FIG. 18A provides an exemplary illustration in which the proximal ends, 252 and 262, of the lobes, 250 and 260, are shaped such as to define a transversely extending void space 292 adjacent the proximal ends, 252 and 262, of the lobes, 250 and 260, respectively, that is more round in shape. FIG. 18B provides an exemplary illustration in which the proximal ends, 252 and 262, of the lobes, 250 and 260, are shaped such as to define a transversely extending void space 292 adjacent the proximal ends, 252 and 262, of the lobes, 250 and 260, respectively, that is more triangular in shape. FIG. 18C provides an exemplary illustration in which the proximal ends, 252 and 262, of the lobes, 250 and 260, are shaped such as to define a transversely extending void space 292 adjacent the proximal ends, 252 and 262, of the lobes, 250 and 260, respectively, that is a diamond shape. FIG. 18D provides an exemplary illustration in which the lobes, 250 and 260, adjacent their proximal ends, 252 and 262, are shaped in such a way as to form a relative V-shape to the void space 270 generally located about the longitudinal axis 12 of the absorbent article 10.

Additional details regarding a lobed absorbent layer 240 can be found in U.S. Publication No. 2014/0316363 to You, et al. which is hereby incorporated by reference thereto in its entirety.

Backsheet Layer:

The backsheet layer 32 is generally liquid impermeable and is the portion of the chassis 20 which faces the garment of the wearer. The backsheet layer 32 can permit the passage of air or vapor out of the chassis 20 while still blocking the passage of liquids. Any liquid impermeable material may generally be utilized to form the backsheet layer 32. The backsheet layer 32 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 32 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 32 can be a polyethylene film such as that obtainable from Pliant Corporation, Schaumburg, Ill., USA. Another example can include calcium carbonate-filled polypropylene film. In still another embodiment, the backsheet layer 32 can be a hydrophobic nonwoven material with water barrier properties such as a nonwoven laminate, an example of which can be a spunbond, meltblown, meltblown, spunbond, four-layered laminate. The backsheet layer 32 can, therefore, be of a single or multiple layer construction, such as of multiple film layers or laminates of film and nonwoven fibrous layers. Suitable backsheet layers 32 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

In various embodiments, such as, for example, illustrated in FIGS. 1-4, the backsheet layer 32 can overlay a garment facing surface 50 of the absorbent system 34 and a portion of each of the longitudinal direction peripheral regions, 54 and 56, of the absorbent system 34. In such embodiments, the topsheet layer 30 can overlay the wearer facing surface 52 of the absorbent system 34 and a portion of each of the longitudinal direction peripheral regions, 54 and 56, of the absorbent system 34. In such embodiments, the longitudinal direction peripheral edges, 90 and 92, of the topsheet layer 30 and the longitudinal direction peripheral edges, 70 and 72, of the backsheet layer 32 can be bonded to each other forming longitudinal direction bond regions, 110 and 112. Each of the longitudinal direction bond regions, 110 and 112, form a portion of the seal 38 between the topsheet layer 30 and the backsheet layer 32 of the chassis 20. In such embodiments, the absorbent article 34 can have transverse direction peripheral regions, 58 and 60, beyond which can extend portions of the topsheet layer 30 and the backsheet layer 32. The transverse direction peripheral edges, 94 and 96, of the topsheet layer 30 can be bonded to the transverse direction peripheral edges, 74 and 76, of the backsheet layer 32 to form transverse direction bond regions, 114 and 116, respectively, which can form a portion of the seal 38 between the topsheet layer 30 and the backsheet layer 32 of the chassis 20. In such embodiments, the longitudinal direction bond regions, 110 and 112, and the transverse direction bond regions, 114 and 116, together form the seal 38 of the chassis 20 of the absorbent article 10.

Referring to FIGS. 9-12, in various embodiments, the backsheet layer 32 can overlay a garment facing surface 50 of the absorbent system 34, each of the longitudinal direction peripheral regions, 54 and 56, of the absorbent system 34, and at least a portion of the wearer facing surface 52 of the absorbent system 34. In such embodiments, the backsheet layer 32 can partially enclose the absorbent system 34 by wrapping around the absorbent system 34 until the longitudinal direction peripheral edges, 70 and 72, of the backsheet layer 32 overlay a portion of the wearer facing surface 52 of the absorbent system 34. In such embodiments, the portions of the backsheet layer 32 which overlay the longitudinal direction peripheral regions, 54 and 56, can form the longitudinal direction side edges, 44 and 46, of the chassis 20. In such embodiments, the topsheet layer 30 can overlay the wearer facing surface 52 of the absorbent system 34 and can partially enclose the absorbent system 34. In such embodiments, the longitudinal direction peripheral edges, 90 and 92, of the topsheet layer 30 and the longitudinal direction peripheral edges, 70 and 72, of the backsheet layer 32 can be bonded to each other forming longitudinal direction bond regions, 110 and 112. Each of the longitudinal direction bond regions, 110 and 112, overlay the wearer facing surface 52 of the absorbent system 34 and form a portion of the seal 38 between the topsheet layer 30 and the backsheet layer 32 of the chassis 20. In such embodiments, the absorbent system 34 can have transverse direction peripheral regions, 58 and 60, beyond which can extend portions of the topsheet layer 30 and backsheet layer 32. The transverse direction peripheral edges, 94 and 96, of the topsheet layer 30 can be bonded to the transverse direction peripheral edges, 74 and 76, of the backsheet layer 32 to form transverse direction bond regions, 114 and 116, respectively, which can form a portion of the seal 38 between the topsheet layer 30 and the backsheet layer 32 of the chassis 20. In such embodiments, the longitudinal direction bond regions, 110 and 112, and the transverse direction bond regions, 114 and 116, together form the seal 38 of the chassis 20 of the absorbent article 10.

Figure 22:
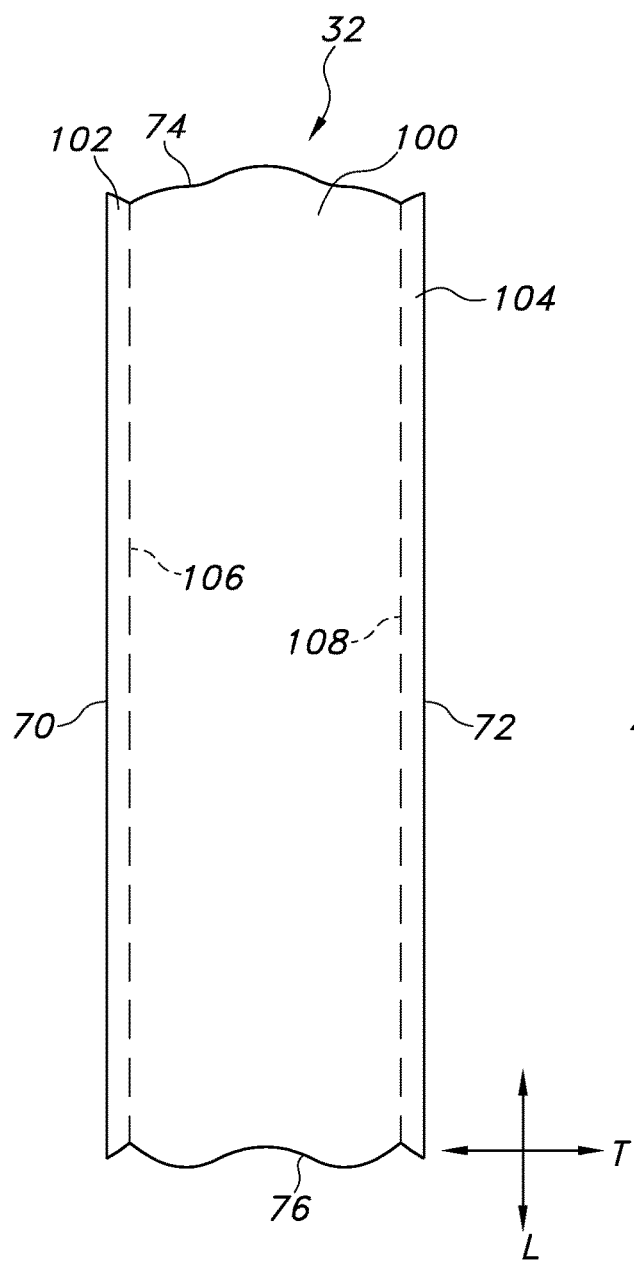
FIG. 22 is a top view of an embodiment of a backsheet layer in an unfolded configuration.
Figure 23:
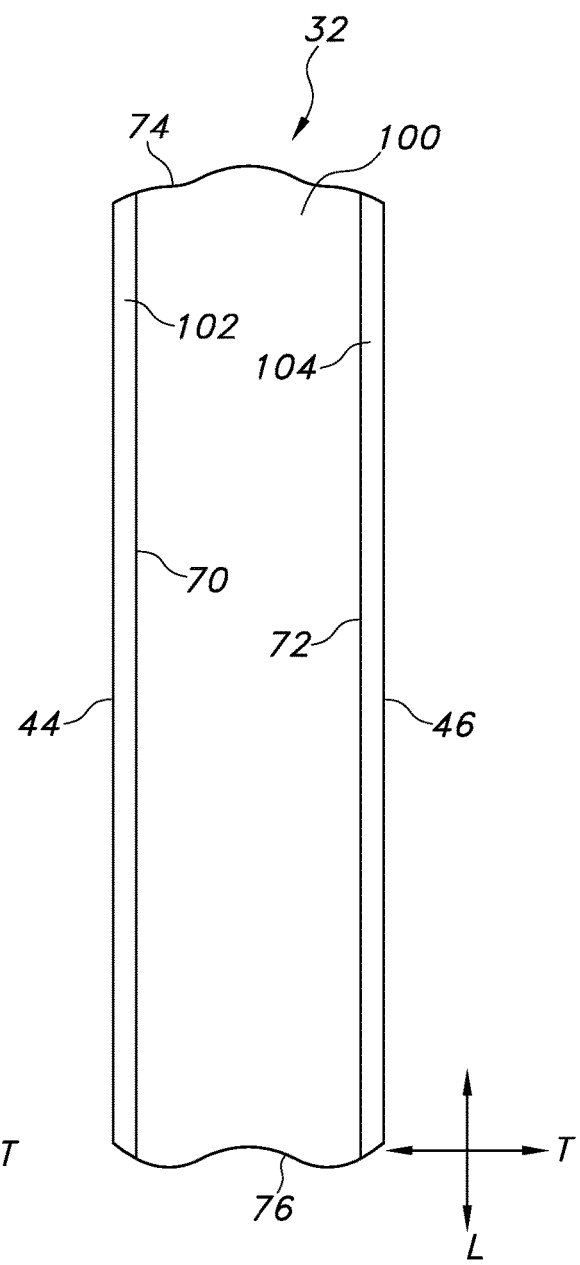
FIG. 23 is a top view of an embodiment of a backsheet layer in a folded configuration.

FIGS. 22 and 23 provide illustrations of an exemplary backsheet layer 32 in an unfolded and folded configuration, respectively. Referring to FIG. 22, the backsheet layer 32 can be in an unfolded and laid flat configuration. The backsheet layer 32 can have a central portion 100 and a pair of opposing longitudinal direction side portions, 102 and 104. The backsheet layer 32, in an unfolded and laid flat configuration can have a width greater than the width of the topsheet layer 30 of the chassis 20. In various embodiments, the side portions, 102 and 104, can each have transverse direction end edges which can correspond in a mirror-image relationship to the configuration of the transverse direction end edges, 74 and 76, of the central portion 100 of the backsheet layer 32. Having a mirror-image correspondence between the transverse direction end edges of the side portions, 102 and 104, and the transverse direction end edges, 74 and 76, of the central portion 100 of the backsheet layer 32 when the backsheet layer 32 is in a flat, unfolded configuration can allow for each of the transverse direction end edges of the side portions, 102 and 104, to correspond to and substantially align with the transverse direction end edges, 74 and 76, of the central portion 100 of the backsheet layer 32 when the backsheet layer 32 is in a folded configuration. As illustrated in FIG. 22, each of the transverse direction end edges, 74 and 76, of the central portion 100 of the backsheet layer 32 has a curvature and the transverse direction end edges of each of the side portions, 102 and 104, have the mirror-image curvature which can correspond with the transverse direction end edges, 74 and 76, when the backsheet layer 32 is in a folded configuration, such as illustrated in FIG. 23.

In the manufacture of the chassis 20 for the absorbent article 10 such as illustrated in FIGS. 9-12, central portion 100 of the backsheet layer 32 can overlay a garment facing surface 50 of the absorbent system 34 and the side portions, 102 and 104, can be re-positioned to wrap around the absorbent system 34 such that the side portions, 102 and 104, can overlay each of the longitudinal direction peripheral regions, 54 and 56, of the absorbent system 34 and the longitudinal direction peripheral edges, 70 and 72, of the backsheet layer 32 can be positioned over a wearer facing surface 52 of the absorbent system 34. The side portions, 102 and 104, can begin to wrap around an absorbent system in the fold areas, 106 and 108. It is to be understood that the fold areas, 106 and 108, can be, but need not be, a single linear fold line in the backsheet layer 32. FIG. 23 provides an illustration of an exemplary embodiment in which the side portions, 102 and 104, of the backsheet layer 32 have been re-positioned to overlay an absorbent system 34 (not shown in FIG. 23). Additional exemplary illustrations of the backsheet layer 32 in such a folded configuration can be seen in FIGS. 19-21. The longitudinal direction peripheral edges, 70 and 72, can then be bonded to the longitudinal direction peripheral edges, 90 and 92, of the topsheet layer 30 to partially enclose the absorbent system 34 and to form a portion of the seal 38 of the chassis 20 of the absorbent article 10.

Figure 24:
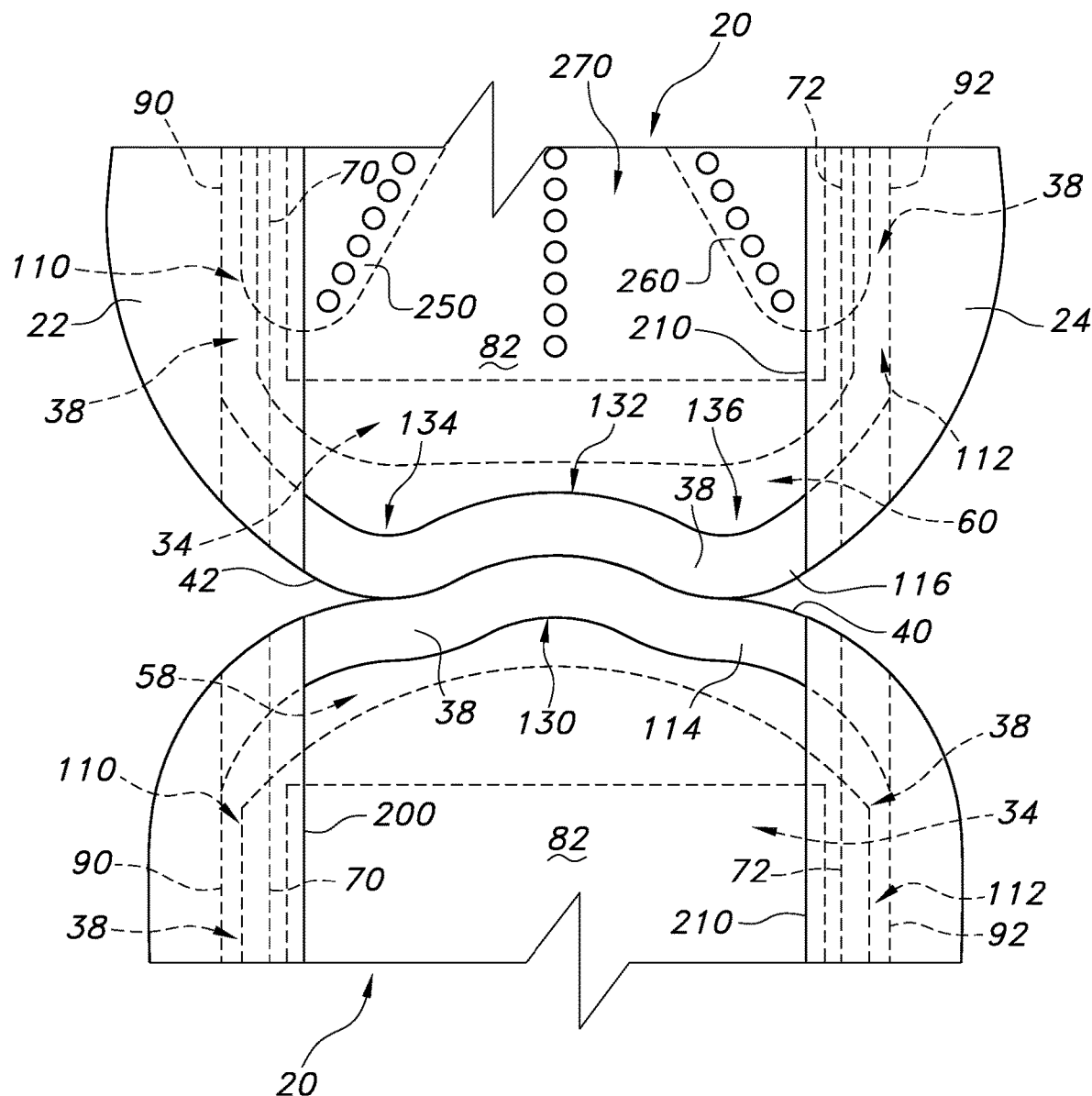
FIG. 24 is a sectional view of a nesting configuration of a first end edge of an absorbent article with a second end edge of the absorbent article.

Nesting Edges:

In various embodiments, the transverse direction end edges, 40 and 42, of the chassis 20 can be linear or can have at least one curve (convex and/or concave) in the transverse direction (T) of the chassis 20. In various embodiments, one of the transverse direction end edges, 40 or 42, can have at least one curve (convex and/or concave) and the other of the transverse direction end edges, 40 or 42, can have at least one curve (convex and/or concave) and the curve of the first transverse direction end edge, 40 or 42, can be positioned into a nesting configuration with the second of the transverse direction end edge, 40 or 42. A curve can be defined as convex or concave when viewed from the perspective of the intersection of the longitudinal axis 12 and the transverse axis 14. FIG. 24 provides a sectional view of an absorbent article 10 in which the transverse direction end edges, 40 and 42, can be positioned into a nesting configuration with each other. As illustrated in FIG. 24, transverse direction end edge 40 can have a convex curve 130 and transverse direction end edge 42 can have a concave curve 132 and two convex curves, 134 and 136. The convex curve 130 of transverse direction end edge 40 can nest between the two convex curves, 134 and 136, of transverse direction end edge 42. The nesting configuration can also position convex curve 130 of transverse direction end edge 40 into an abutment with concave curve 132 of transverse direction end edge 42.

Flexure Features:

In various embodiments, the chassis 20 can have at least one flexure feature 140. The at least one flexure feature 140 can be positioned in the chassis 20 in a location intended to be worn towards the posterior of the wearer. The relative position of the at least one flexure feature 140 can be seen in FIGS. 1-4. The at least one flexure feature 140 can help initiate and influence shaping of the absorbent article 10 into a raised and tented configuration. The raised and tented configuration can conform to the gluteal cleft and can move in response to the alternating movement of the wearer's legs thereby helping the absorbent article 10 stay in place for leakage protection and comfort. In various embodiments, the at least one flexure feature 140 can create different bend resistances across the chassis 20 of the absorbent article 10. The at least one flexure feature 140 can be created by physical discontinuities in the chassis 20 and/or elements of the chassis 20. For example, the at least one flexure feature 140 can be created by pre-folding, scoring, indenting, perforating, embossing, bonding, or combinations thereof. In various embodiments, the at least one flexure feature 140 can be created by scoring, folding, indenting, perforating, embossing, or bonding one or more layers of the chassis 20 of the absorbent article 10. In various embodiments, the at least one flexure feature 140 can be created with changes in elevation and/or density to the chassis 20 and/or elements of the chassis 20. Optionally, the at least one flexure feature 140 helps initiate and regulate dynamic movement in the posterior region of the absorbent article 10.

In various embodiments, the flexure feature 140 can associate with the lobed absorbent layer 240 and the void space 270 defined by the lobed absorbent layer 240. In various embodiments, the flexure feature 140 of the chassis 20 can have a first flexure element 142 which may extend in a direction generally parallel to the longitudinal axis 12 of the chassis 20 of the absorbent article 10. In such embodiments, the first flexure element 142 may be present, in the depth direction (Z) of the absorbent article 10, in the topsheet layer 30 and any other layer of the absorbent article 10 except the lobed absorbent layer 240. The first flexure element 142 may be positioned within the void space 270 defined by the lobed absorbent layer 240. In various embodiments, the flexure feature 140 of the chassis 20 can have a second flexure element 144 which can be spaced transversely outward from the first flexure element 142 in a first direction 16. The second flexure element 144 can define a first side portion 150 of the chassis 20. The first side portion 150 is positioned transversely outward from the second flexure element 144 in the first direction 16. In various embodiments, the flexure feature 140 of the chassis 20 can have a third flexure element 146 which can be spaced transversely outward from the first flexure element 142 in a second direction 18 which is opposite the first direction 16. The third flexure element 146 can define a second side portion 152 of the chassis 20. The second side portion 152 is positioned transversely outward from the third flexure element 146 in the second direction 18. In various embodiments, the second flexure element 144 and the third flexure element 146 can substantially align with the lobe interior edges, 300 and 310, of the lobes, 250 and 260, respectively. In such embodiments, the second flexure element 144 and the third flexure element 146 can be present in the topsheet layer 30 and any other layer of the absorbent article 10 as deemed suitable as well as in the lobes, 250 and 260, respectively. In such embodiments, the second flexure element 144 and the third flexure element 146 can be present in a similar shape and/or configuration as the interior edges, 300 and 310, of the lobes, 250 and 260. For example, the interior edges, 300 and 310, of the lobes, 250 and 260, respectively, can diverge rearward at an angle relative to the longitudinal axis 12 which can be from about 1, 2, 3, 5, 7, or 10 degrees to about 15, 20, 25, 30, 35, 40, or 45 degrees. In such exemplary embodiments, the second flexure element 144 and the third flexure element 146 can be present within the lobes, 250 and 260, of the lobed absorbent layer 240 and can substantially align with the interior edges, 300 and 310, of the lobes, 250 and 260, respectively, and can also diverge rearward at an angle relative to the longitudinal axis 12 which can be from about 1, 2, 3, 5, 7 or 10 degrees to about 15, 20, 25, 30, 35, 40, or 45 degrees. Without being bound by theory, it is believed that the association of the flexure feature 140 with the lobed absorbent layer 240 can maintain the absorbent article 10 in a raised and tented configuration while providing a comfortable fit to the wearer of the absorbent article 10.

In various embodiments, the absorbent article 10 can have a secondary flexure feature 320, such as illustrated, for example, in FIG. 1. The secondary flexure feature 320 can be positioned in a posterior region of the absorbent article 10. The relative position of the secondary flexure feature 320 can be seen in FIG. 1. The secondary flexure feature 320 can help initiate and influence shaping of the absorbent article 10 into a raised and tented configuration. In various embodiments, the secondary flexure feature 320 can create different bend resistances across the chassis 20 of the absorbent article 10. The secondary flexure feature 320 can be created by physical discontinuities in the chassis 20 and/or elements of the chassis 20. For example, the secondary flexure feature 320 can be created by pre-folding, scoring, indenting, perforating, embossing, bonding, or combinations thereof. In various embodiments, the secondary flexure feature 320 can be created by scoring, folding, indenting, perforating, embossing, or bonding one or more layers of the chassis 20 of the absorbent article 10. In various embodiments, the secondary flexure feature 320 can be created with changes in elevation and/or density to the chassis 20 and/or elements of the chassis 20. Optionally, the second flexure feature 320 helps initiate and regulate dynamic movement in the posterior region of the absorbent article 10. The secondary flexure feature 320 can extend in a direction generally parallel to the transverse axis 14 of the chassis 20 of the absorbent article 10. In various embodiments, the secondary flexure feature 320 can be positioned in the transverse direction void space 292 of the void space 270. In such embodiments, the secondary flexure feature 320 may be present, in the depth direction (Z) of the absorbent article 10, in the topsheet layer 30 and any other layer of the absorbent article 10 except the lobed absorbent layer 240 in the depth direction (Z). The secondary flexure feature 320 may be present within the generally transversely extending void space 292 of the lobed absorbent layer 240.

Figure 13:
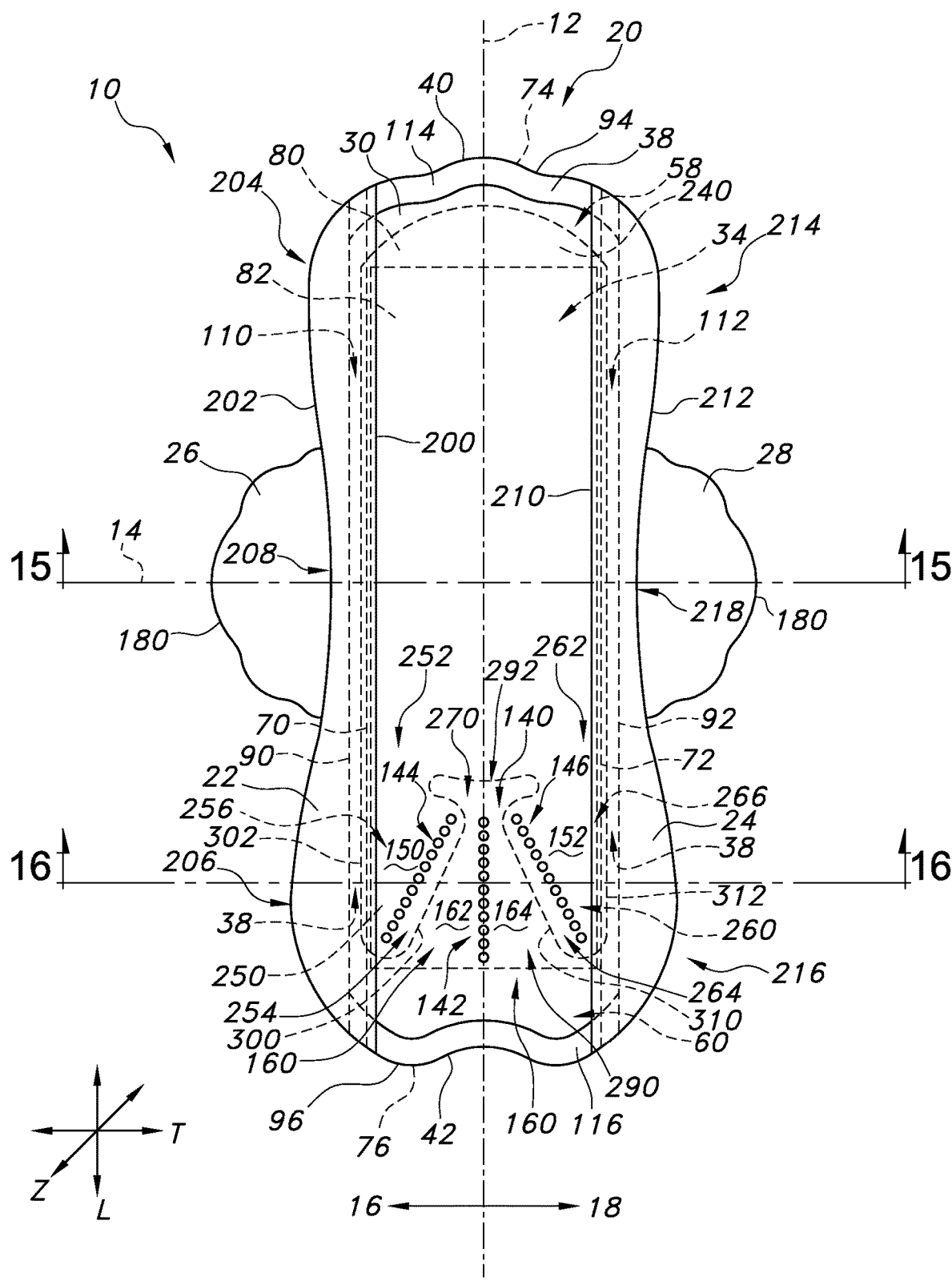
FIG. 13 is a top view of an embodiment of an absorbent article.
Figure 14:
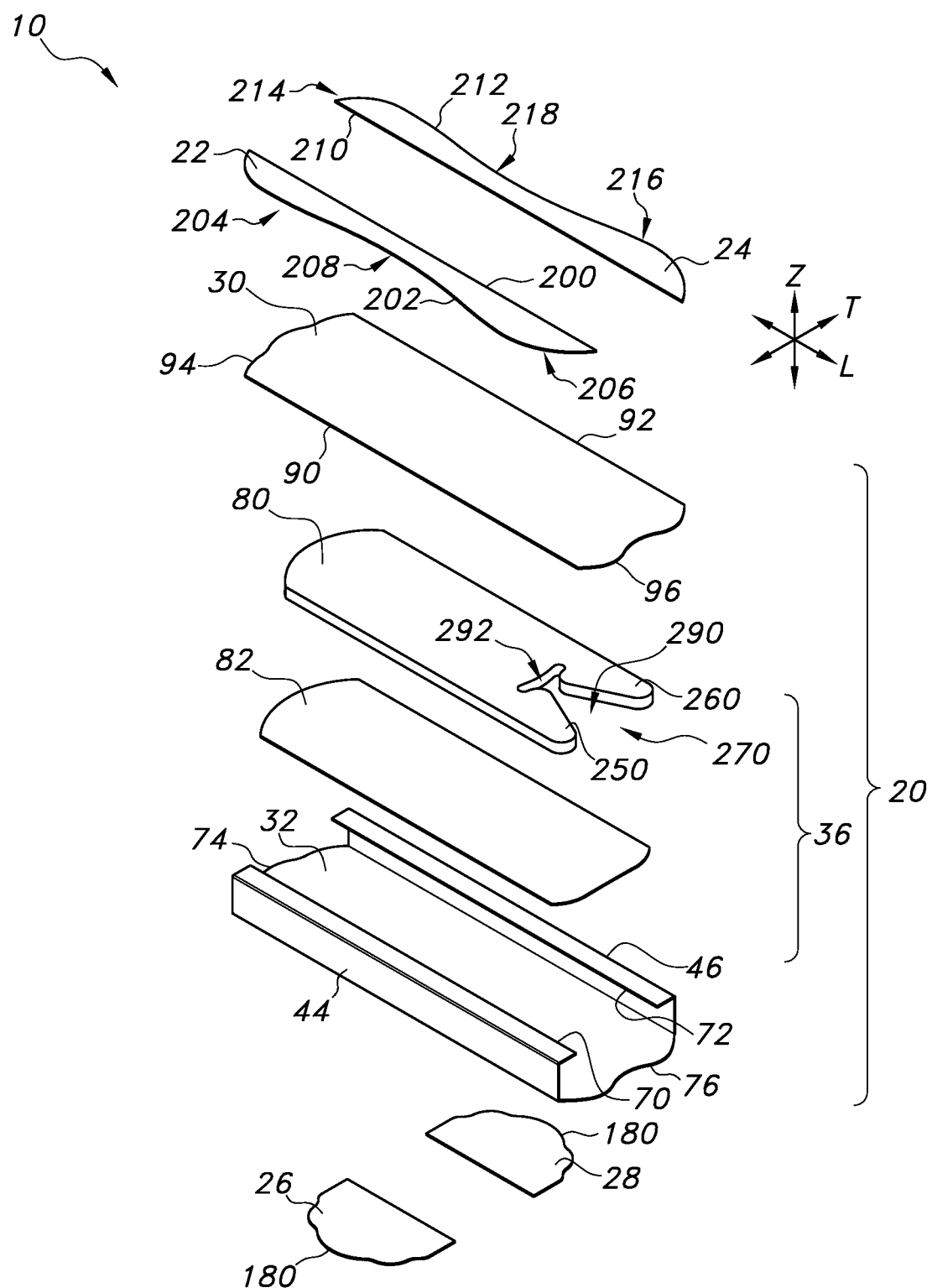
FIG. 14 is an exploded perspective view of the absorbent article of FIG. 13.
Figure 15:
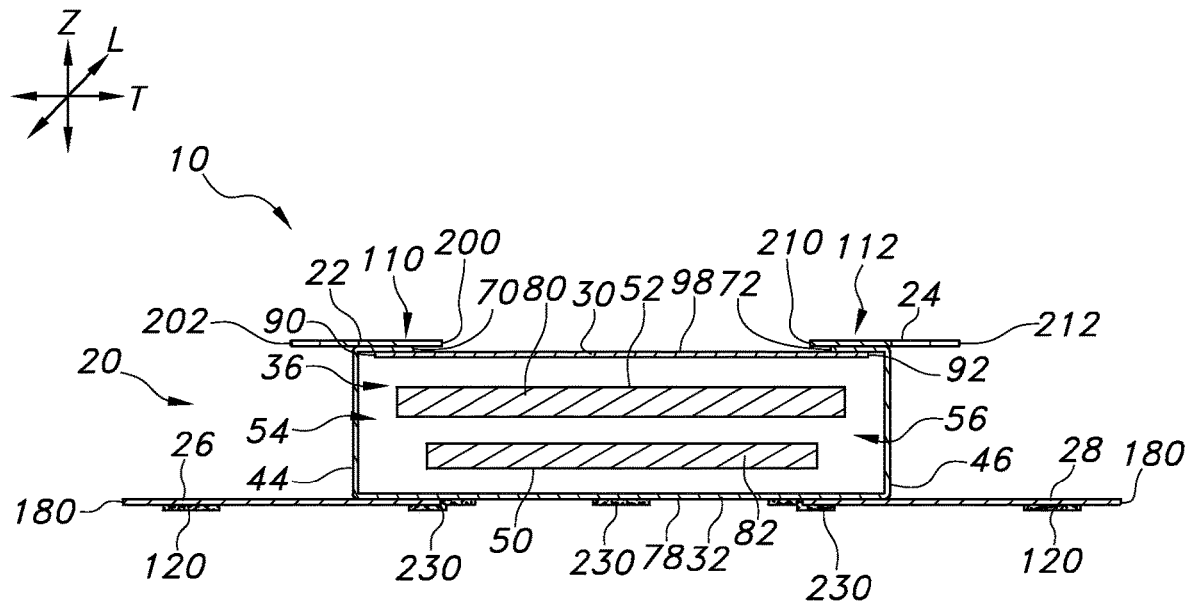
FIG. 15 is an exploded cross-sectional view of the absorbent article of FIG. 13 taken along line 15-15.
Figure 16:
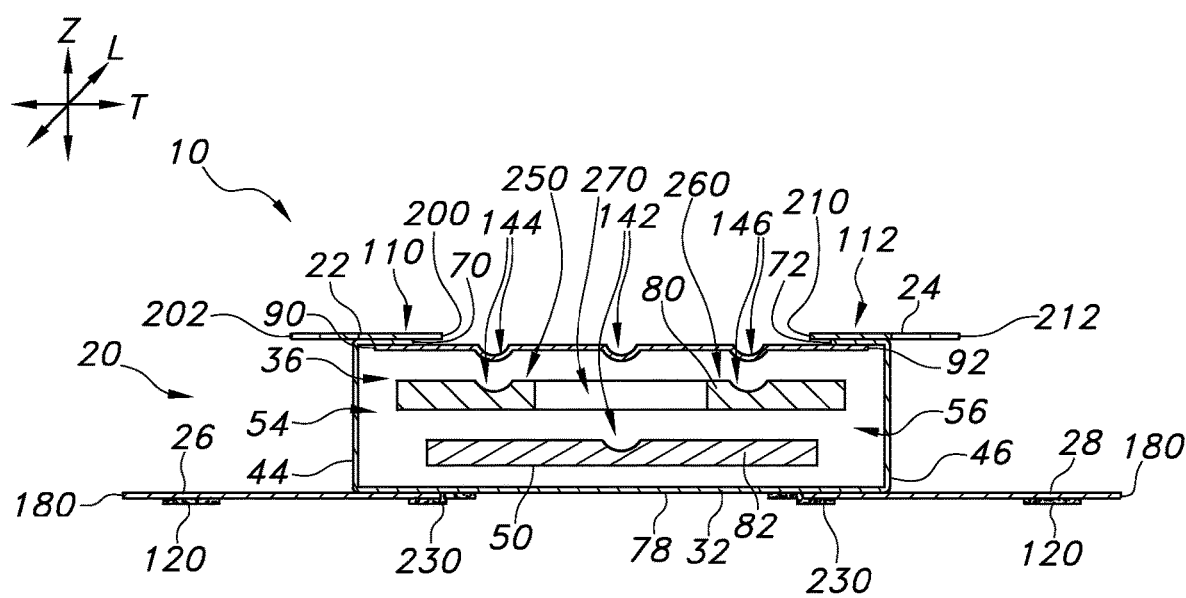
FIG. 16 is an exploded cross-sectional view of the absorbent article of FIG. 13 taken along line 16-16.
Figure 25:
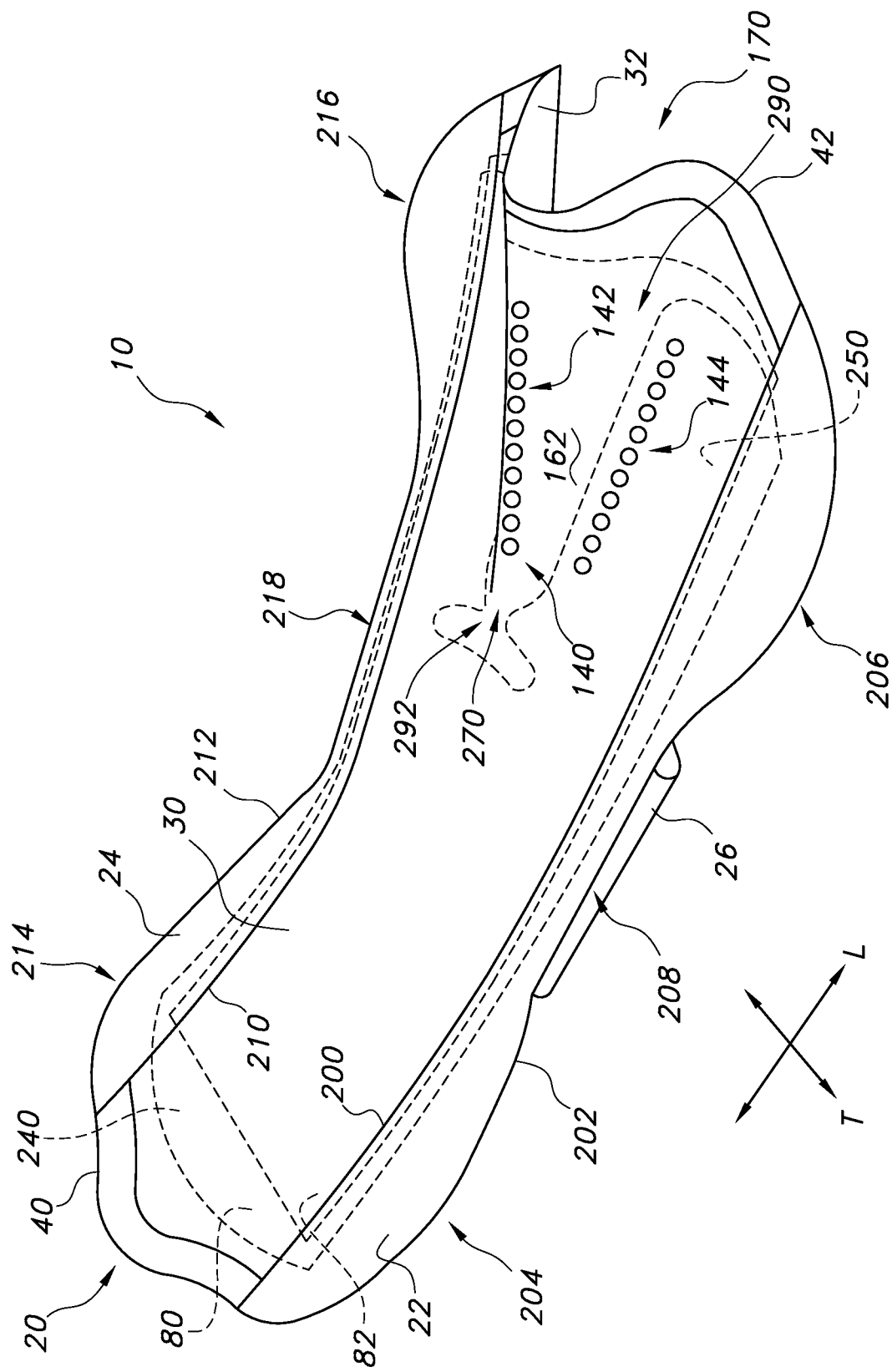
FIG. 25 is a perspective view of the absorbent article of FIG. 13 in a tented configuration.
Figure 26:
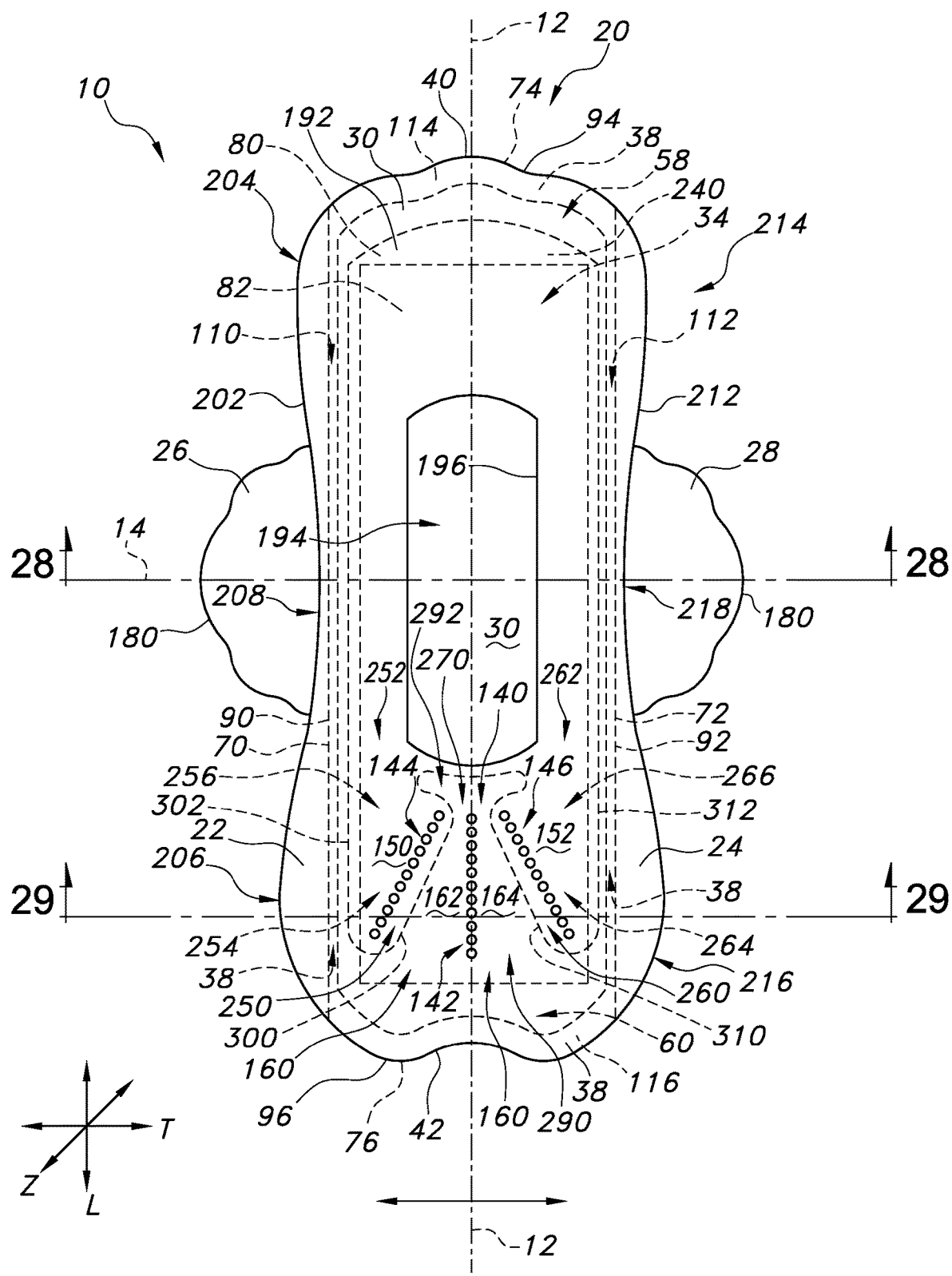
FIG. 26 is a top view of an embodiment of an absorbent article.
Figure 27:
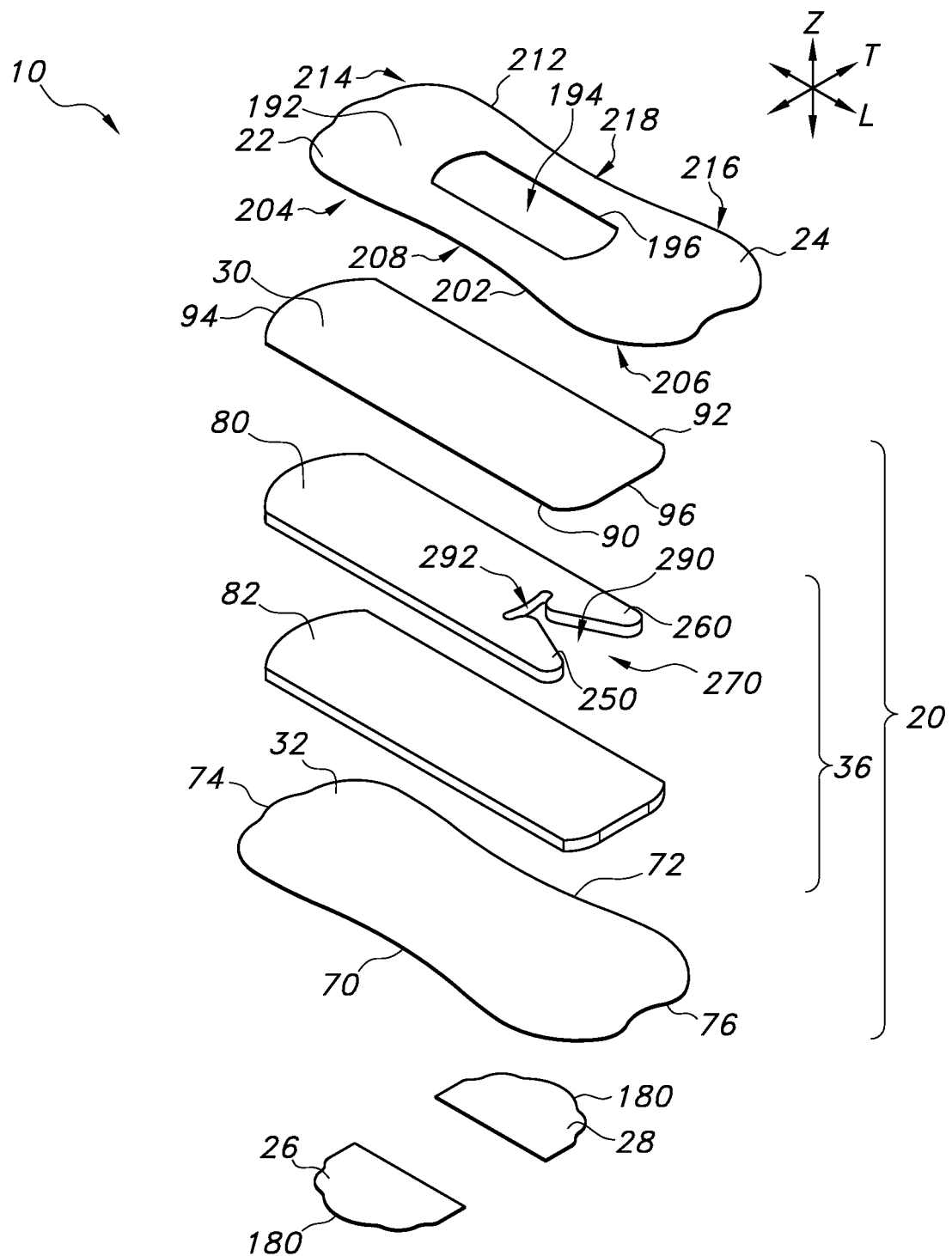
FIG. 27 is an exploded perspective view of the absorbent article of FIG. 26.
Figure 28:
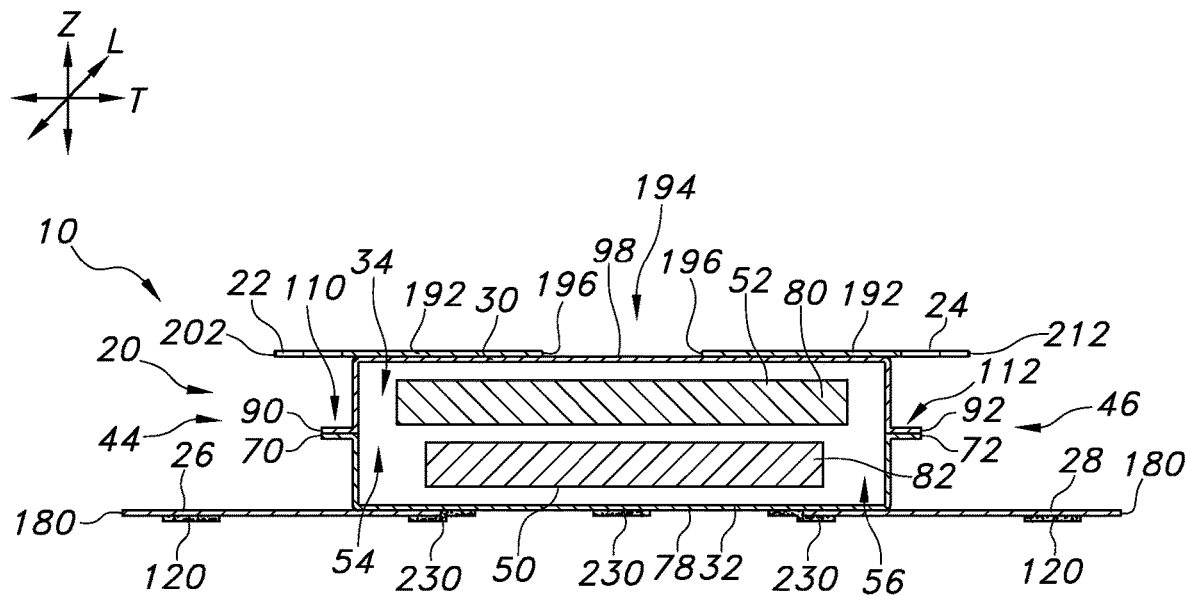
FIG. 28 is an exploded cross-sectional view of the absorbent article of FIG. 26 taken along line 28-28.
Figure 29:
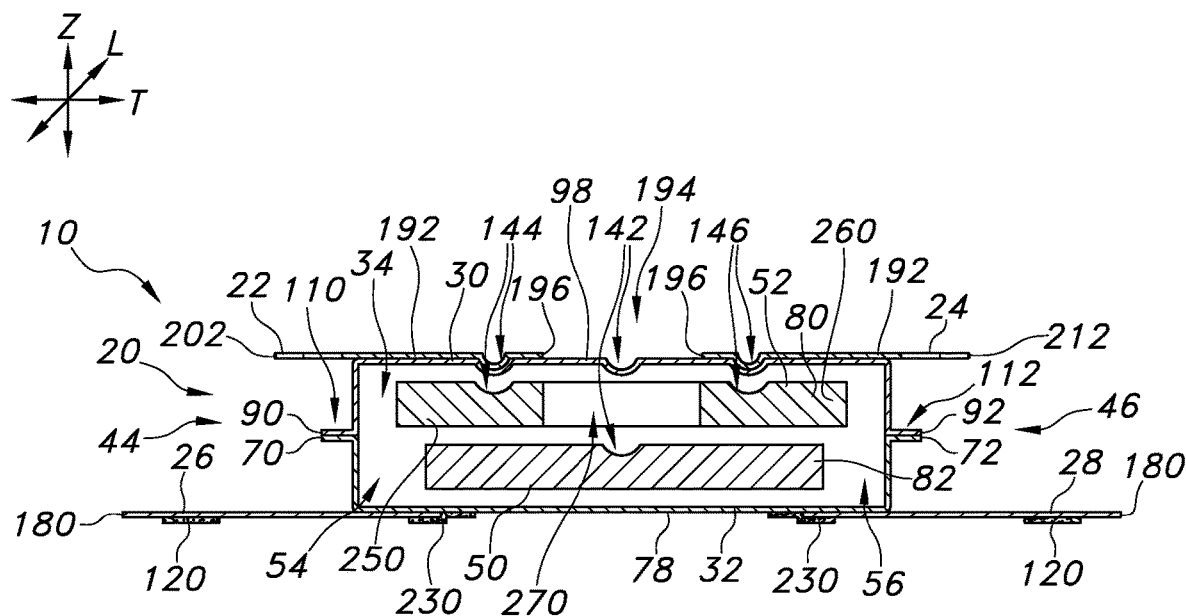
FIG. 29 is an exploded cross-sectional view of the absorbent article of FIG. 26 taken along line 29-29.

Referring to FIG. 25, the absorbent article 10 of FIG. 13 is illustrated in a tented configuration 170. The tented configuration 170 is formed in the posterior region of the absorbent article 10 when the absorbent article 10 is subjected to lateral compressive force. The tented configuration 170 is formed relative to the first flexure element 142, the second flexure element 144, and the third flexure element 146 (not visible in this view). The tented configuration 170 is adapted to conform to the perineal region posterior to the vulva for the purpose of intercepting body exudates moving along the skin and/or preventing body exudates from following the body beyond the vulva region. The tented configuration 170 includes the topsheet layer 30, the backsheet layer 32, and the absorbent system 34 positioned between the topsheet layer 30 and the backsheet layer 32. The tented configuration 170 is shaped by the first flexure element 142, the second flexure element 144, and the third flexure element 146. The tented configuration 170 can be dynamic due to a lack of a garment attachment 230 on the exterior surface 78 of the backsheet layer 32 of the absorbent article 10 in the area of the backsheet layer 32 below the flexure feature 140. The lack of the garment attachment 230 in such an area can result in a lack of attachment between the absorbent article 10 and the wearer's undergarment in such an area thereby allowing the absorbent article 10 to be dynamic in use and form a tented configuration 170. The second flexure element 144 and the third flexure element 146 can define a dynamic region 160 of the chassis 20 and of the absorbent article 10 there between. The second flexure element 144 and the first flexure element 142 define a first side 162 of the dynamic region 160. The third flexure element 146 and the first flexure element 142 define a second side 164 of the dynamic region 160.

The first flexure element 142 is believed to act as a lever to assist in lifting the tented configuration 170 to provide contact against the perineum and posterior vulva. The lifting force is generated by the reciprocating motion of the legs. This reciprocating motion alternately pumps the first side 162 of the dynamic region 160 and the second side 164 (not visible in this view) of the dynamic region 160 towards the gluteal cleft. Generally, the compressive force of the legs alternates when walking or running. In these situations, the compressive force alternates between the two sides of the absorbent article 10. The compression force can be transferred to the dynamic region 160 in the posterior region of the absorbent article 10. The first side 162 and the second side 164 are free to move in response to these forces because the backsheet layer 32 is free of a garment attachment 230 in the area of the backsheet layer 32 below the flexure feature 140.

In various embodiments, it may be desirable to provide a tented configuration 170 in which the absorbent article 10 has a "flat" tented configuration (not shown) rather than the "peak" tented configuration such as illustrated in FIG. 25. Such a "flat" configuration may be provided by incorporating more than one first flexure element 142 in the depth direction (Z) of the absorbent article 10 and within the void space 270 defined by the lobed absorbent layer 240. In such an embodiment, each of the first flexure elements 142 can diverge rearward (i.e., towards the posterior transverse direction end edge) at an angle relative to the longitudinal axis 12 of the absorbent article 10.

The resultant tented configuration 170 of the absorbent article 10 can be sized as deemed suitable. The configuration of the lobed absorbent layer 240, the presence of the flexure feature 140, the optional presence of the secondary flexure feature 320, the longitudinal length of concave curve 132 and the positioning of a garment attachment 230 can impact the configuration of the absorbent article 10 when in a tented configuration. The void space 270 defined by the lobed absorbent layer 240 can provide an area of the absorbent system 34 in which material has been removed from the absorbent system 34, thereby allowing for a more comfortable fit to the wearer of the absorbent article 10 when the absorbent article 10 is in use. Provision of a flexure feature 140, and association of the flexure feature 140 with the lobed absorbent layer 240 and the void space 270 as described, can reinforce the positioning of the lobes, 250 and 260, of the lobed absorbent layer 240 and can maintain that positioning when the absorbent article 10 is in the tented configuration 170. To enable the absorbent article 10 to move into the tented configuration, the backsheet layer 32 can be free of a garment attachment 230 in the area directly below, in the depth direction (Z), the longitudinally extending void space 290 of the void space 270. The longitudinal extent of the tented configuration of the absorbent article 10 can be any longitudinal length as deemed suitable. To provide comfort to the wearer of the absorbent article 10 by providing a "stop" to the longitudinal extent of the tented configuration, a transversely extending void space 292 can be incorporated into the lobed absorbent layer 240. Optionally, the transversely extending void space 292 can have positioned therein a secondary flexure feature 320. To further encourage the termination of the longitudinal extent of the tented configuration, the backsheet layer 32 can have a garment attachment 230 positioned in the area directly beneath, in the depth direction (Z), the transversely extending void space 292 of the void space 270. The longitudinal direction length of the concave curve 132 can also be sized as deemed suitable to minimize rubbing of absorbent article 10 materials against the skin of the wearer of the absorbent article 10. Each of these elements can be sized and configured as deemed suitable to provide for an absorbent article 10 which is comfortable to wear.

Side Covers:

In various embodiments, the absorbent article 10 can have an opposing pair of non-integral side covers, 22 and 24. In various embodiments, such as, for example, illustrated in FIGS. 5-8, 13-16, and 19-21, the non-integral side covers, 22 and 24, can be provided as two separate components which can be bonded to the absorbent article 10. Each side cover, 22 and 24, can extend in the longitudinal direction (L) and can extend the length of the chassis 20 of the absorbent article 10 from the first transverse direction end edge 40 to the second transverse direction end edge 42 of the chassis 20. In such embodiments, the side covers, 22 and 24, can be positioned over the longitudinal direction bond regions, 110 and 112, which form a portion of the seal of the chassis 20. The side covers, 22 and 24, can be bonded to a portion of the exterior surface 78 of the backsheet layer 32 and/or a portion of the wearer facing surface 98 of the topsheet layer 30. For example, referring to FIGS. 13-16, the side covers, 22 and 24, can be bonded to at least a portion of the exterior surface 78 of the backsheet layer 32. As an additional example, referring to FIGS. 5-8, the side covers, 22 and 24, can be bonded to at least a portion of the wearer facing surface 98 of the topsheet layer 30. Such side covers, 22 and 24, can be adhesively, thermally, ultrasonically, or otherwise bonded to the chassis 20. Traditional absorbent article construction adhesive may be used to bond the side covers, 22 and 24, to the chassis 20. In such a positioning, the side covers, 22 and 24, can provide a softer and less irritating material to be in contact with the skin of the wearer than the exterior surface 78 of the backsheet layer 32. In such a positioning, the side covers, 22 and 24, can prevent the longitudinal direction bond regions, 110 and 112, from coming into direct contact with the skin of the wearer. In such a positioning, when the wings, 26 and 28, of the absorbent article 10 are wrapped about a wearer's undergarment, the side covers, 22 and 24, which are independent from the wings, 26 and 28, can remain undistorted by the folding of the wings, 26 and 28, about the wearer's undergarment.

In various embodiments, such as embodiments in which the side covers, 22 and 24, are provided as two separate components bonded to the absorbent article 10, such as, for example, illustrated in FIGS. 5-8, each of the side covers, 22 and 24, can have a longitudinal direction edge, 200 and 210, respectively, which is positioned closer to the longitudinal axis 12 of the absorbent article 10 and can have a longitudinal direction distal edge, 202 and 212, respectively, which is positioned further from the longitudinal axis 12 of the absorbent article 10 than the longitudinal direction edge, 200 and 210, respectively. In various embodiments, while the longitudinal direction edges, 200 and 210, of the side covers, 22 and 24, respectively, can be bonded to the absorbent article 10, the distal edges, 202 and 212, of the side covers, 22 and 24, respectively, can remain unbonded to the absorbent article 10. In various embodiments, each of the longitudinal direction edges, 200 and 210, can be linear. In various embodiments, each of the longitudinal direction edges, 200 and 210, can have a curve (convex and/or concave). In various embodiments, each of the longitudinal direction distal edges, 202 and 212, can be linear. In various embodiments, each of the longitudinal direction distal edges, 202 and 212, can have a curve (convex and/or concave). In various embodiments, each of the longitudinal direction edges, 200 and 210, can be linear and each of the longitudinal direction distal edges, 202 and 212, can have a curve (convex and/or concave). In various embodiments, each of the longitudinal direction edges, 200 and 210, and each of the longitudinal direction distal edges, 202 and 212, can have a curve (convex and/or concave). In various embodiments, each of the longitudinal direction edges, 200 and 210, can have a curve (convex and/or concave) and each of the longitudinal direction distal edges, 202 and 212, can be linear. In various embodiments, each of the longitudinal direction edges, 200 and 210, and each of the longitudinal direction distal edges, 202 and 212, can be linear.

In various embodiments, such as, for example, illustrated in FIGS. 26-29, the non-integral side covers, 22 and 24, can be extensions of, and integral with, a cover bridge 192 which can be bonded to the absorbent article 10. Each side cover, 22 and 24, and the cover bridge 192 can extend in the longitudinal direction (L) and can extend the length of the chassis 20 of the absorbent article 10 from the first transverse direction end edge 40 to the second transverse direction end edge 42 of the chassis 20. In such embodiments, the side covers, 22 and 24, can be positioned over the longitudinal direction bond regions, 110 and 112, which form a portion of the seal of the chassis 20 and the cover bridge 192 can be positioned over at least the topsheet layer 30 of the chassis 20. The cover bridge 192 can be constructed of any material described herein as suitable for the topsheet layer 30. In various embodiments, the cover bridge 192 can be provided with an opening 194, defined by a perimeter 196, through which the topsheet layer 30 can be exposed. The opening 194 can be positioned at various positions along the longitudinal axis 12 and transverse axis 14 as deemed suitable for the intake of body exudates into the absorbent article 10. The opening 194 can have any shape as well as any length and width as deemed suitable for the intake of body exudates into the absorbent article 10.

In various embodiments, the cover bridge 192 and/or the extensions of the cover bridge 192 forming the side covers, 22 and 24, can be bonded to a portion of the exterior surface 78 of the backsheet layer 32 and/or a portion of the wearer facing surface 98 of the topsheet layer 30. For example, referring to FIGS. 26-29, the cover bridge 192 can be bonded to the topsheet layer 30 of the absorbent article 10 and the side covers, 22 and 24, as extensions of the cover bridge 192, can have a portion which remains unbonded to the absorbent article 10. It is to be understood that in various embodiments in which the chassis 20 of the absorbent article 10 is constructed such as illustrated, for example, in FIGS. 13-16, in which the backsheet layer 32 partially encloses the absorbent system 34, the cover bridge 192 can be bonded to a portion of the wearer facing surface 98 of the topsheet layer 30 and/or a portion of the exterior surface 78 of the backsheet layer 32 of the chassis 20 of the absorbent article 10. In such embodiments, the extensions of the cover bridge 192 forming the side covers, 22 and 24, can have a portion which can remain unboned to the absorbent article 10. The cover bridge 192 and/or a portion of the side covers, 22 and 24, can be adhesively, thermally, ultrasonically, or otherwise bonded to the chassis 20. Traditional absorbent article construction adhesive may be used to bond the cover bridge 192 and/or a portion of the side covers, 22 and 24, to the chassis 20. In such a positioning, the side covers, 22 and 24, can provide a softer and less irritating material to be in contact with the skin of the wearer than the exterior surface 78 of the backsheet layer 32. In such a positioning, the side covers, 22 and 24, can prevent the longitudinal direction bond regions, 110 and 112, from coming into direct contact with the skin of the wearer. In such a positioning, when the wings, 26 and 28, of the absorbent article 10 are wrapped about a wearer's undergarment, the side covers, 22 and 24, which are independent from the wings, 26 and 28, can remain undistorted by the folding of the wings, 26 and 28, about the wearer's undergarment.

In various embodiments, such as embodiments in which the side covers, 22 and 24, are provided as extensions of a cover bridge 192, each of the side covers, 22 and 24, can have a longitudinal direction distal edge, 202 and 212, respectively, which is positioned further from the longitudinal axis 12 of the absorbent article 10. In various embodiments, each of the longitudinal direction distal edges, 202 and 212, can be linear. In various embodiments, each of the longitudinal direction distal edges, 202 and 212, can have a curve (convex and/or concave).

In various embodiments, whether provided as two separate components or as extensions of a cover bridge 192, the longitudinal direction distal edges, 202 and 212, of the side covers, 22 and 24, respectively, can each have at least one concave curve, such as concave curves, 204 and 214, respectively, and at least one convex curve, such as convex curves, 208 and 218, respectively. In various embodiments, the longitudinal direction distal edges, 202 and 212, of the side covers, 22 and 24, respectively, can each at least two convex curves. In such embodiments, longitudinal direction distal edge 202 can have convex curves, 204 and 206, and longitudinal direction distal edge 212 can have convex curves, 214 and 216. In such embodiments, convex curves, 204 and 206, can be separated by concave curve 208. In such embodiments, convex curves, 214 and 216, can be separated by concave curve 218. A curve can be defined as convex or concave when viewed from the perspective of the intersection of the longitudinal axis 12 and the transverse axis 14.

In various embodiments such as when the side covers, 22 and 24, are provided as two separate components, the transverse direction (T) width of the side covers, 22 and 24, as measured between the longitudinal direction edges, 200 and 210, respectively, and the maximum point of convex curves, 204 and 214, respectively, can be the same as or smaller than the transverse direction (T) width of the side covers, 22 and 24, as measured between the longitudinal direction edges, 200 and 210, respectively, and the maximum point of convex curves, 206 and 216, respectively. In various embodiments such as when the side covers, 22 and 24, are provided as extensions of cover bridge 192, the longitudinal direction distal edges, 202 and 212, in the area of convex curves, 204 and 214, respectively, can substantially align with the longitudinal direction distal edges, 202, and 212, in the area of convex curves, 206 and 216, respectively, or they can be closer to the longitudinal axis 12 of the absorbent article 10 than the longitudinal direction distal edges, 202 and 212, in the area of the convex curves, 206 and 216.

In various embodiments, the side covers, 22 and 24, can be constructed from a material which can be the same as or different from the material of the topsheet layer 30 of the chassis 20. In various embodiments, the topsheet layer 30 of the chassis 20 can be at least partially hydrophilic and the side covers, 22 and 24, may be inherently hydrophobic or may be treated with a hydrophobic coating. In various embodiments, the side covers, 22 and 24, can be constructed from a material which can be the same as or different from the material of the cover bridge 192, if present. In various embodiments, the cover bridge 192, can be at least partially hydrophilic and the extensions forming the side covers, 22 and 24, may be inherently hydrophobic or may be treated with a hydrophobic coating.

Different nonwoven, woven, or film sheet materials may be utilized as the side covers, 22 and 24. The selection of such side cover, 22 and 24, materials can vary based upon the overall desired attributes of the side covers, 22 and 24. For example, it may be desired to have a hydrophilic material in the topsheet layer 30 of the chassis 20 and hydrophobic-barrier type materials in the side covers, 22 and 24, to prevent leakage and increase a sense of dryness in the area of the side covers, 22 and 24. Either of the topsheet layer 30 of the chassis 20 and/or the side covers, 22 and 24, may be treated with surfactants and/or skin-health benefit agents, as are well known in the art.

Such longitudinally directed side covers, 22 and 24, can be of a single or multi-layered construction. In various embodiments, the side covers, 22 and 24, can be adhesively or otherwise bonded laminates. In various embodiments, the side covers, 22 and 24, can be a through air bonded carded web material. In various embodiments, the side covers, 22 and 24, can be a single layer of material, such as through air bonded carded web, without a second layer of material, such as a barrier film material, present. In various embodiments, the side covers, 22 and 24, can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as a polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall side cover, 22 and 24, design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 10 side edges when viewed from above the absorbent article 10. In various embodiments, the side covers, 22 and 24, can be laminates such as a spunbond-meltblown-meltblown-spunbond layer ("SMMS") laminate, spunbond-film laminate, or alternatively, other nonwoven laminate combinations.

Figure 30:
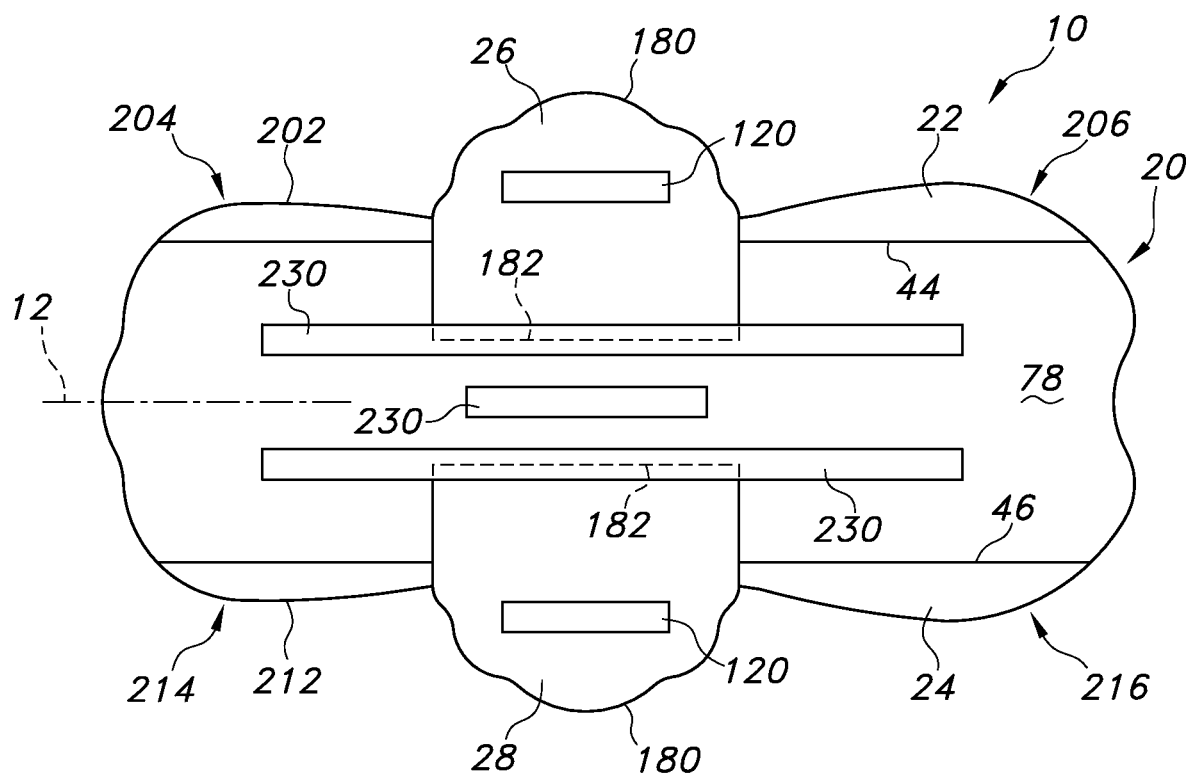
FIG. 30 is a bottom view of an embodiment of an absorbent article.
Figure 31:
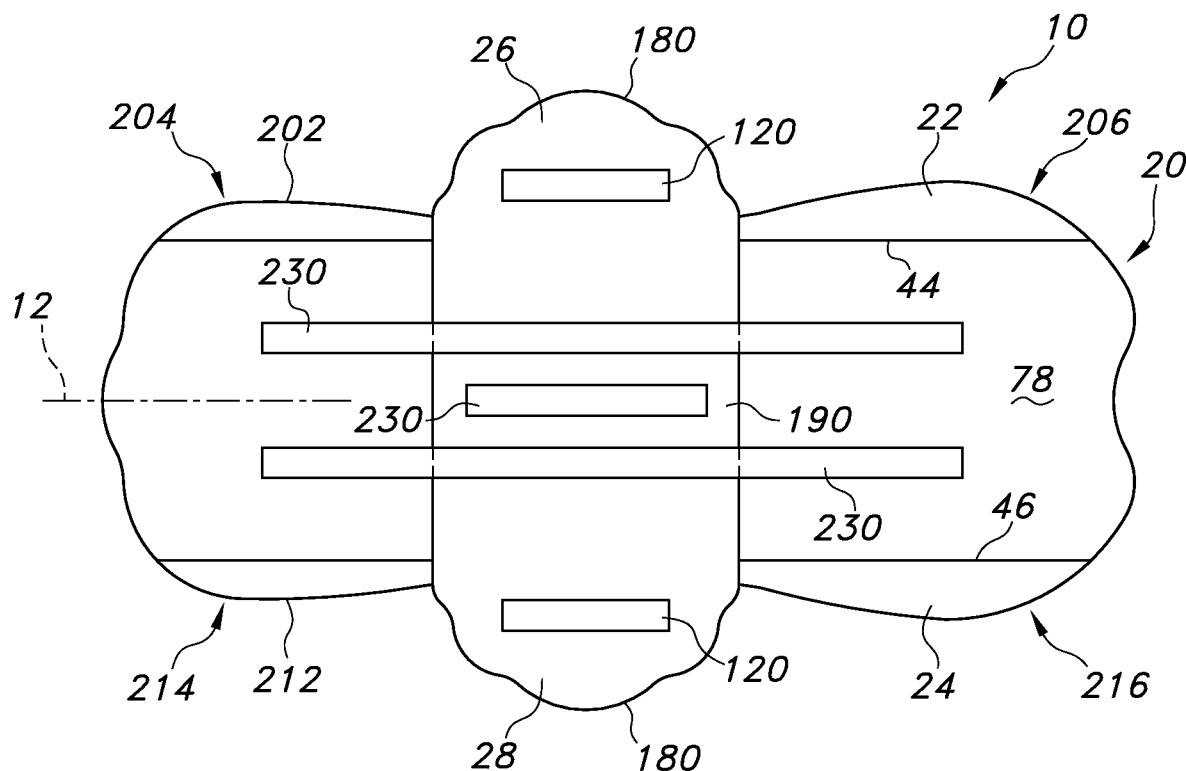
FIG. 31 is a bottom view of an embodiment of an absorbent article.

Wings:

The absorbent article 10 can have a pair of non-integral wings, 26 and 28, extending outwardly in the transverse direction (T) from the absorbent article 10. The wings, 26 and 28, can be bonded to the exterior surface 78 of the backsheet layer 32 of the chassis 20 of the absorbent article 10. Referring to FIG. 30, in various embodiments, the wings, 26 and 28, can be two separate components bonded to the exterior surface 78 of the backsheet layer 32. In such an embodiment, each wing, 26 and 28, can have a distal edge 180 extending outward in a transverse direction (T) from the absorbent article 10 and proximal edge 182 positioned closer to and/or adjacent to the longitudinal axis 12 of the absorbent article 10 or between the longitudinal direction side edges, 44 and 46, and the longitudinal axis 12 of the absorbent article. The proximal edge 182 can be permanently bonded to the backsheet layer 32 of the absorbent article 10 while the distal edge 180 of the wings, 26 and 28, can remain unbonded to the backsheet layer 32 of the absorbent article 10. Referring to FIG. 31, in various embodiments, the wings, 26 and 28, can be extensions of, and integral with, a wing bridge 190 which can be bonded to the backsheet layer 32 and extend in a transverse direction across the width of the chassis 20 of the absorbent article 10. In such an embodiment, each wing can have a distal edge 180 extending outward in a transverse direction (T) from the absorbent article 10. The wing bridge 190 can be permanently bonded to the backsheet layer 32 of the absorbent article in the vicinity of the longitudinal axis 12 of the absorbent article 10 and the distal edges 180 of each of the wings, 26 and 28, can remain unbonded to the backsheet layer 32 of the absorbent article 10.

In various embodiments, whether the wings, 26 and 28, are provided as two separate components or as extensions from a wing bridge 190, the wings, 26 and 28, can be provided in any manner as deemed suitable so as to be adjustable when the absorbent article 10 is positioned for usage within a wearer's undergarment. For example, a permanent bonding of the wings, 26 and 28, to the absorbent article 10 can be located in the vicinity of the longitudinal axis 12 of the absorbent article 10. In various embodiments, the wings, 26 and 28, could be provided with temporary and releasable bonds with the backsheet layer 32 a distance away from the permanent bond in the immediate vicinity of the longitudinal axis 12. The temporary and releasable bonds can be broken by the wearer of the absorbent article 10 to customize and adjust the amount of wing coverage needed for placement of the absorbent article 10 in their undergarment. In various embodiments, the wings, 26 and 28, could be provided with pleats which can be releasably bonded together to remain in a folded configuration prior to usage of the absorbent article 10. The releasably folded configuration of the pleats can allow the wearer of the absorbent article 10 to extend, or refrain from extending, the wings, 26 and 28, as needed to conform to the width of the undergarment of the wearer.

The wings, 26 and 28, can be constructed from materials described above with respect to the topsheet layer 20 and the backsheet layer 22. The wings, 26 and 28, can be formed independently and separately attached to an intermediate section of the absorbent article 10. Wings, 26 and 28, that are made independent of the other components of the absorbent article 10 can be bonded to a portion of the backsheet layer 32. The wings, 26 and 28, can be bonded to the absorbent article 10 in locations which may not interfere with and/or hinder further manipulation of the absorbent article 10, such as, for example, the folding of the absorbent article 10 by the manufacturer to place the absorbent article 10 into the final packaged configuration. Examples of processes for manufacturing absorbent articles 10 and wings, 26 and 28, include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No. 2004/0040650 to Venturino, et al., and international publication WO1997/040804 to Emenaker, et al., each of which are hereby incorporated by reference thereto in its entirety. Each of the wings, 26 and 28, can have an attachment aid 120, such as, for example, a garment attachment adhesive or a hook, to keep the absorbent article 10 securely and properly positioned in the undergarment. The wings, 26 and 28, can wrap around the crotch region of the wearer's undergarment to aid in securing the absorbent article 10 to the wearer's undergarment when in use. Each wing, 26 and 28, can fold under the crotch region of the wearer's undergarment and the attachment aid 120 can either form a secure attachment to the opposite wing, 26 or 28, or directly to the surface of the wearer's undergarment.

Garment Attachment:

The absorbent article 10 can be provided with a garment attachment 230 which can be located on an exterior surface 78 of the backsheet layer 32 for attachment of the absorbent article 10 to a wearer's undergarment. The garment attachment 230 can be provided in any suitable arrangement and/or pattern on the exterior surface of the backsheet layer 32 as deemed suitable. In various embodiments, such as embodiments in which the absorbent article 10 has a flexure feature 140, the backsheet layer 32 can be substantially free of a garment attachment 230 in the area of the backsheet layer 32 which is below the flexure feature 140. In such embodiments wherein the backsheet layer 32 has an area which is substantially free of a garment attachment 230, that area of the absorbent article 10 is substantially unattached to the wearer's undergarment and can move in response to the alternating movement of the legs thereby inducing the absorbent article 10 to re-position into a tented configuration 170. The garment attachment 230 can include any suitable attachment mechanism, such as, but not limited to, adhesive, cohesive, hooks, snaps, clips, or the like, or combinations thereof.

In various embodiments, the garment attachment 230 can be provided in any suitable amount on the exterior surface 78 of the backsheet layer 32 as deemed suitable. In various embodiments, the garment attachment 230 can be applied over the complete area of the exterior surface 78 of the backsheet layer 32. In various embodiments, the garment attachment 230 can be provided on less than the complete area of the exterior surface 78 of the backsheet layer 32. In various embodiments, the garment attachment 230 can be provided in any pattern as deemed suitable, such as, for example, stripes, swirls, dots, or the like, and combinations thereof.

In various embodiments, the garment attachment 230 can be provided in an amount that can correspond to the transverse direction (T) width of the crotch region of a wearer's undergarment. In various embodiments, an absorbent article 10 can be intended to be worn in an undergarment with a wide transverse direction (T) crotch region and the absorbent article 10 can be provided with a garment attachment 230 in an amount which can correspond to the transverse direction (T) width of the wide crotch region of the undergarment. In various embodiments, an absorbent article 10 can be intended to be worn in an undergarment with a narrow transverse direction (T) crotch region and the absorbent article 10 can be provided with a garment attachment 230 in an amount which can correspond to the transverse direction (T) narrow width of the crotch region of the undergarment. In such embodiments, the absorbent article 10 can have a wearer facing surface (topsheet layer 30 and side covers, 22 and 24) which can have a transverse direction (T) width which can be wider than the transverse direction (T) width of the absorbent system 34 which can be wider than the transverse direction (T) width of the garment attachment 230.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article characterized by comprising:
   a. a longitudinal direction, a transverse direction, and a depth direction;
   b. a longitudinal axis and a transverse axis wherein the absorbent article is asymmetrical about the transverse axis;
   c. a chassis comprising:
      i. a first transverse direction end edge and a second transverse direction end edge;
      ii. a topsheet layer comprising a first longitudinal direction peripheral edge and a second longitudinal direction peripheral edge;
      iii. a backsheet layer comprising a first longitudinal direction peripheral edge and a second longitudinal direction peripheral edge;
      iv. an absorbent system positioned between the topsheet layer and the backsheet layer, the absorbent system comprising a garment facing surface, a wearer facing surface, a first longitudinal direction peripheral region and a second longitudinal direction peripheral region, and at least two absorbent layers, wherein at least one of the absorbent layers of the absorbent system is a lobed absorbent layer comprising a first lobe and a second lobe wherein the first and second lobe define a longitudinally extending void space in the lobed absorbent layer, and wherein the lobed absorbent layer further comprises a transversely extending void space;
      v. a first longitudinal direction bond region wherein the first longitudinal direction peripheral edge of the topsheet layer is bonded to the first longitudinal direction peripheral edge of the backsheet layer; and
      vi. a second longitudinal direction bond region wherein the second longitudinal direction peripheral edge of the topsheet layer is bonded to the second longitudinal direction peripheral edge of the backsheet layer;
      vii. at least one flexure feature wherein the at least one flexure feature comprises at least one flexure element extending in a direction generally parallel to the longitudinal axis and wherein the at least one flexure element is positioned within the void space; and
      viii. a secondary flexure feature extending in a direction generally parallel to the transverse axis and positioned within the transversely extending void space; and
   d. a first non-integral wing and a second non-integral wing, each of the first and second non-integral wings bonded to the backsheet layer.

2. The absorbent article of claim 1 further comprising a first side cover bonded to the chassis in the region of the first longitudinal direction bond region and a second side cover bonded to the chassis in the region of the second longitudinal direction bond region.

3. The absorbent article of claim 2 wherein each of the first side cover and the second side cover is bonded to an exterior surface of the backsheet layer.

4. The absorbent article of claim 2 wherein each of the first side cover and the second side cover extend between the first transverse direction end edge and the second transverse direction end edge of the chassis.

5. The absorbent article of claim 2 wherein each of the first side cover and the second side cover have at least one concave region and at least one convex region.

6. The absorbent article of claim 1 wherein the first non-integral wing and the second non-integral wing are separate components from each other.

7. The absorbent article of claim 1 wherein the first non-integral wing and the second non-integral wing are integral with a bridge which is bonded to the backsheet layer.

8. The absorbent article of claim 1 wherein at least one of the first transverse direction end edge and the second transverse direction end edge has at least one concave region.

9. The absorbent article of claim 1 wherein the at least one flexure feature comprises a second flexure element, the second flexure element spaced in the transverse direction outward from the first flexure element and positioned at an angle relative to the longitudinal axis.

10. The absorbent article of claim 9 wherein the second flexure element is aligned with an interior side edge of at least one of the lobes of the lobed absorbent layer.

11. The absorbent article of claim 1 further comprising a garment attachment on an exterior surface of the backsheet layer wherein the backsheet layer is substantially free of the garment attachment in an area of the backsheet layer positioned below the flexure feature in the depth direction of the absorbent article.

12. The absorbent article of claim 1 wherein the absorbent system further comprises at least one additional layer selected from a surge layer, a fluid intake layer, a transfer delay layer and a distribution layer.

* * * * *